(12) United States Patent
Alemparte-Gallardo et al.

(10) Patent No.: US 8,318,940 B2
(45) Date of Patent: Nov. 27, 2012

(54) NAPHTHYRIDIN-2 (1 H)-ONE COMPOUNDS USEFUL AS ANTIBACTERIALS

(75) Inventors: Carlos Alemparte-Gallardo, Research Triangle Park, NC (US); David Barros-Aguirre, Research Triangle Park, NC (US); Monica Cacho-Izquierdo, Research Triangle Park, NC (US); Jose Maria Fiandor Roman, Research Triangle Park, NC (US); Jose Luis Lavandera Diaz, Research Triangle Park, NC (US); Modesto Jesús Remuiñan-Blanco, Research Triangle Park, NC (US)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 13/144,507

(22) PCT Filed: Jan. 15, 2010

(86) PCT No.: PCT/EP2010/050452
§ 371 (c)(1),
(2), (4) Date: Dec. 21, 2011

(87) PCT Pub. No.: WO2010/081874
PCT Pub. Date: Jul. 22, 2010

(65) Prior Publication Data
US 2012/0115899 A1    May 10, 2012

(30) Foreign Application Priority Data

Jan. 15, 2009  (WO) ................. PCT/EP2009/050436
Jul. 17, 2009  (EP) ..................................... 09382116

(51) Int. Cl.
*A61K 31/44* (2006.01)
*C07D 471/02* (2006.01)

(52) U.S. Cl. ........................................ 546/113; 514/300
(58) Field of Classification Search .................. 546/123; 514/300
See application file for complete search history.

(56) References Cited

U.S. PATENT DOCUMENTS

2011/0319424 A1* 12/2011 Alemparte-Gallardo 514/255.05

FOREIGN PATENT DOCUMENTS

| EP | 2 022 793 | 2/2009 |
|---|---|---|
| WO | WO 2007/138974 | 12/2007 |
| WO | WO 2009/090222 | 7/2009 |

* cited by examiner

*Primary Examiner* — Janet Andres
*Assistant Examiner* — Heidi Reese
(74) *Attorney, Agent, or Firm* — Bonnie L. Deppenbrock

(57) ABSTRACT

Compounds of Formula (I),

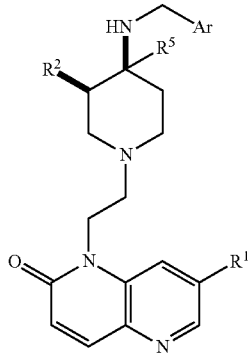

wherein substituents $R^1$, $R^2$ and $R^5$ are as defined, and Ar represents substituted phenyl, pyridyl, pyridazinyl, pyrimidinyl, pyrazinyl, thiazolyl, furanyl, imidazolyl and thiophenyl substituted by a hydroxyalkyl substituent and an optional other substituent; compositions containing them, their use in therapy, including their use as antibacterials, for example in the treatment of tuberculosis, and methods for the preparation of such compounds, are provided.

18 Claims, No Drawings

NAPHTHYRIDIN-2 (1 H)-ONE COMPOUNDS USEFUL AS ANTIBACTERIALS

This application is filed pursuant to 35 U.S.C. §371 as a United States National Phase Application of International Patent Application Serial No. PCT/EP2010/050452 filed Jan. 15, 2010, which claims priority to PCT/EP2009/050436 filed 15 Jan. 2009, and to European Patent Application No. 09382116.3 filed in the European Cooperation Treaty Organization on Jul. 17, 2009, the contents of which are incorporated herein by reference.

FIELD OF THE INVENTION

This invention relates to compounds, compositions containing them, their use in therapy, including their use as antibacterials, for example in the treatment of tuberculosis, and methods for the preparation of such compounds.

BACKGROUND OF THE INVENTION

PCT patent publications WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO2006002047, WO2006014580, WO2006010040, WO2006017326, WO2006012396, WO2006017468, WO2006020561, WO2006081179, WO2006081264, WO2006081289, WO2006081178, WO2006081182, WO01/25227,WO02/40474, WO02/07572, WO2004024712, WO2004024713, WO2004035569, WO2004087647, WO2004089947, WO2005016916, WO2005097781, WO2006010831, WO2006021448, WO2006032466, WO2006038172, WO2006046552, WO2006099884, WO2006105289, WO2006081178, WO2006081182, WO2007016610, WO2007081597, WO2007071936, WO2007115947, WO2007118130, WO2007122258 and WO2007/138974 disclose quinoline, naphthyridine, morpholine, cyclohexane, piperidine and piperazine derivatives and also tricyclic condensed ring compounds, having antibacterial activity. WO2004104000 discloses tricyclic condensed ring compounds capable of selectively acting on cannabinoid receptors.

Synthetic drugs for treating tuberculosis (TB) have been available for over half a century, but incidences of the disease continue to rise world-wide. In 2004, it is estimated that 24,500 people developed active disease and close to 5,500 died each day from TB (World Health Organization, Global Tuberculosis Control: Surveillance, Planning, Financing. WHO Report 2006, Geneva, Switzerland, ISBN 92-4 156314-1). Co-infection with HIV is driving the increase in incidence (Williams, B. G.; Dye, C. *Science,* 2003, 301, 1535) and the cause of death in 31% of AIDS patients in Africa can be attributed to TB (Corbett, E. L.; Watt, C. J.; Catherine, J.; Walker, N.; Maher D.; Williams, B. G.; Raviglione, M. C.; Dye, C. *Arch. Intl. Med.,* 2003, 163, 1009, Septkowitz, A.; Raffalli, J.; Riley, T.; Kiehn, T. E.; Armstrong, D. *Clin. Microbiol. Rev.* 1995, 8, 180). When coupled with the emergence of multi-drug resistant strains of *Mycobacterium tuberculosis* (MDR-TB), the scale of the problem is amplified. It is now more than a decade since the WHO declared TB "a global health emergency" (World Health Organization, Global Tuberculosis Control: Surveillance, Planning, Financing. WHO Report 2006, Geneva, Switzerland, ISBN 92-4 156314-1).

The limitations of tuberculosis therapy and prevention are well known. The current available vaccine, BCG was introduced in 1921 and fails to protect most people past childhood. Patients who do become infected with active disease currently endure combination therapy with isoniazid, rifampin, pyrazinamide and ethambutol for two months and then continue taking isoniazid and rifampin for a further four months. Daily dosing is required and poor compliance drives the emergence and spread of multi-drug-resistant strains, which are challenging to treat. A recently published detailed review discusses many aspects of TB such as pathogenesis, epidemiology, drug discovery and vaccine development to date (Nature Medicine, Vol 13(3), pages 263-312).

Shorter courses of more active agents which can be taken less frequently and which present a high barrier to the emergence of resistance, i.e. agents which are effective against multi-drug resistant strains of TB (MDR-TB), are urgently required. There is therefore a need to discover and develop new chemical entities to treat TB (recent synthetic leads are reviewed in: Ballell, L.; Field, R. A.; Duncan, K.; Young, R. J. *Antimicrob. Agents Chemother.* 2005, 49, 2153).

DETAILED DESCRIPTION OF THE INVENTION

The present invention provides a compound of Formula (I) or a pharmaceutically acceptable salt, solvate or N-oxide thereof:

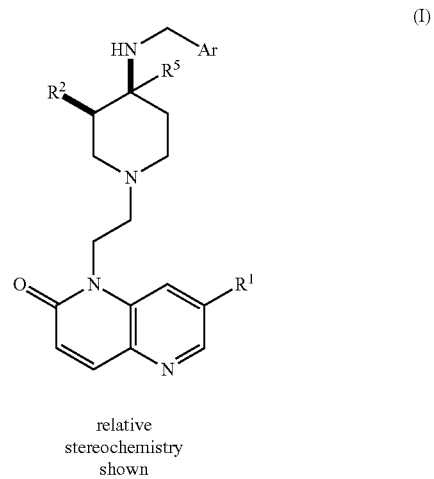

(I)

relative stereochemistry shown

Wherein in Formula (I):
$R^1$ represents hydrogen; halo; or $C_{1-3}$alkoxy-;
$R^2$ represents hydrogen or hydroxy;
Ar represents a group selected from: phenyl, pyridyl, pyridazinyl, pyrimidinyl, pyrazinyl, thiazolyl, furanyl, imidazolyl and thiophenyl;
wherein
Ar is substituted by a first substituent $R^3$, wherein $R^3$ represents $C_{1-5}$ hydroxyalkyl;
Ar is optionally substituted by a second substituent $R^4$ selected from halo, $CF_3$, $C_{1-3}$ alkyl, nitro and $C_{1-3}$ alkoxy-;
and if $R^2$ is hydrogen then $R^5$ is hydrogen or $C_{1-3}$ alkyl, and if $R^2$ is hydroxyl then $R^5$ is hydrogen.

The invention further provides a pharmaceutical composition comprising a compound of Formula (I), or a pharmaceutically acceptable salt, solvate or N-oxide thereof, and one or more pharmaceutically acceptable carriers, excipients or diluents.

The invention also provides a method of treatment of tuberculosis in mammals, particularly in man, which method comprises the administration to a mammal in need of such treatment an effective amount of a compound of Formula (I), or a pharmaceutically acceptable salt, solvate or N-oxide thereof.

This invention further provides a method of treatment of bacterial infections in mammals, particularly in man, which method comprises the administration to a mammal in need of such treatment an effective amount of a compound of formula (I), or a pharmaceutically acceptable salt, solvate or N-oxide thereof.

The invention further provides a compound of Formula (I), or a pharmaceutically acceptable salt, solvate or N-oxide thereof, for use in therapy.

The invention yet further provides a compound of Formula (I), or a pharmaceutically acceptable salt, solvate or N-oxide thereof, for use in the treatment of tuberculosis in mammals, particularly in man.

The invention yet further provides a compound of Formula (I), or a pharmaceutically acceptable salt, solvate or N-oxide thereof, for use in the treatment of bacterial infections in mammals, particularly in man.

The invention still further provides the use of a compound of Formula (I), or a pharmaceutically acceptable salt, solvate or N-oxide thereof, in the manufacture of a medicament for use in the treatment of tuberculosis in mammals, particularly in man.

The invention still further provides the use of a compound of Formula (I), or a pharmaceutically acceptable salt, solvate or N-oxide thereof, in the manufacture of a medicament for use in the treatment of bacterial infections in mammals, particularly in man.

The invention also provides a pharmaceutical composition comprising a compound of Formula (I), or a pharmaceutically acceptable salt, solvate or N-oxide thereof, and one or more pharmaceutically acceptable carriers, excipients or diluents, for use in the treatment of tuberculosis in mammals, particularly in man.

The invention also provides a pharmaceutical composition comprising a compound of Formula (I), or a pharmaceutically acceptable salt, solvate or N-oxide thereof, and one or more pharmaceutically acceptable carriers, excipients or diluents, for use in the treatment of bacterial infections in mammals, particularly in man.

In one aspect of the invention, when Ar represents phenyl, the substituent $R^3$ and optional substituent $R^4$ occur in the meta- or para- positions relative to the point of attachment of Ar to the remainder of the molecule.

In one aspect of the invention, when $R^2$ represents hydroxy, the absolute stereochemistry of the compound of Formula (I), or a pharmaceutically acceptable salt, solvate or N-oxide thereof, is

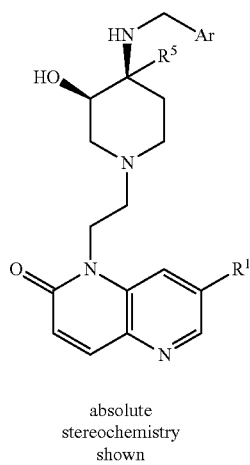

absolute
stereochemistry
shown

In one aspect of the invention, Ar represents a group selected from: phenyl, pyridazinyl, pyridiminyl, pyrazinyl, thiazolyl, furanyl and thiophenyl.

In another aspect of the invention Ar is pyridinyl.

In another aspect of the invention Ar is a 3-pyridinyl substituent and the $C_{1-5}$ hydroxyalkyl group $R^3$ is in the 6-position relative to the ring nitrogen.

In another aspect of the invention the $C_{1-5}$ hydroxyalkyl group $R^3$ is hydroxymethyl.

In another aspect of the invention, the substituent $R^4$ is present.

In another aspect of the invention, the substituent $R^4$ is present and is halo, for example chloro or bromo.

In another aspect Ar is 5-chloro-6-(hydroxymethyl)-3-pyridinyl.

In one aspect, compounds which are useful in the present invention are the pharmaceutically acceptable salts of a compound of Formula (I).

In one aspect, compounds which are useful in the present invention include those mentioned in the examples and their pharmaceutically acceptable salts, solvates or N-oxides.

In another aspect, compounds which are useful in the present invention include:
1-{2-[4-({[5-chloro-6-(hydroxymethyl)-3-pyridinyl]methyl}amino)-1-piperidinyl]ethyl}-7-fluoro-1,5-naphthyridin-2(1H)-one;
1-{2-[4-({[5-chloro-6-(hydroxymethyl)-3-pyridinyl]methyl}amino)-1-piperidinyl]ethyl}-7-fluoro-1,5-naphthyridin-2(1H)-one hydrochloride;
1-{2-[(3R,4S)-4-({[5-chloro-6-(hydroxymethyl)-3-pyridinyl]methyl}amino)-3-hydroxy-1-piperidinyl]ethyl}-7-fluoro-1,5-naphthyridin-2(1H)-one;
1-{2-[(3R,4S)-4-({[5-chloro-6-(hydroxymethyl)-3-pyridinyl]methyl}amino)-3-hydroxy-1-piperidinyl]ethyl}-7-fluoro-1,5-naphthyridin-2(1H)-one hydrochloride;
1-{2-[4-({[5-chloro-6-(hydroxymethyl)-3-pyridinyl]methyl}amino)-1-piperidinyl]ethyl}-7-(methyloxy)-1,5-naphthyridin-2(1H)-one;
1-{2-[4-({[5-bromo-6-(hydroxymethyl)-3-pyridinyl]methyl}amino)-1-piperidinyl]ethyl}-7-fluoro-1,5-naphthyridin-2(1H)-one,
1-{2-[(3R,4S)-4-({[5-chloro-6-(hydroxymethyl)-3-pyridinyl]methyl}amino)-3-hydroxy-1-piperidinyl]ethyl}-7-(methyloxy)-1,5-naphthyridin-2(1H)-one;
and
1-{2-[(3R,4S)-4-({[5-chloro-6-(hydroxymethyl)-3-pyridinyl]methyl}amino)-3-hydroxy-1-piperidinyl]ethyl}-7-(methyloxy)-1,5-naphthyridin-2(1H)-one hydrochloride.

Terms and Definitions

The term "alkyl" as used herein refers to a straight or branched hydrocarbon group containing the stated number number of carbon atoms. For example, "$(C_{1-3})$ alkyl" as used herein refers to a straight or branched hydrocarbon group having 1 to 3 carbon atoms. Examples of $(C_{1-3})$alkyl groups include methyl, ethyl, n-propyl, iso-propyl.

The term "$C_{1-5}$ hydroxyalkyl" as used herein refers to a straight or branched chain hyroxy-substituted alkyl group having 1 to 5 carbon atoms, wherein alkyl is as defined above. Examples of $C_{1-5}$ hydroxyalkyl groups include hydroxymethyl, hydroxyethyl, n-hydroxypropyl, iso-hydroxypropyl.

The term "halo" as used herein refers to fluoro, chloro, bromo and iodo substituents. In one aspect, the term "halo" as used herein refers to fluoro, chloro and bromo substituents. In another aspect, the term "halo" as used herein refers to chloro, bromo and iodo substituents.

The term "$(C_{1-3})$alkoxy" as used herein refers to a straight or branched chain O-alkyl group having 1 to 3 carbon atoms, wherein alkyl is as defined above. Examples of $(C_{1-3})$alkoxy groups include, methoxy, ethoxy, propoxy and isopropoxy.

The term "compounds of the invention" as used herein means a compound of Formula (I) or a pharmaceutically acceptable salt, solvate or N-oxide thereof. The term "a compound of the invention" means any one of the compounds of the invention as defined above.

Furthermore, it will be understood that phrases such as "a compound of Formula (I) or a pharmaceutically acceptable salt, solvate or N-oxide thereof" or "compounds of the invention" are intended to encompass the compound of Formula (I), a pharmaceutically acceptable salt, solvate or N-oxide of the compound of Formula (I), or any pharmaceutically acceptable combination of these. Thus by way of non-limiting example used here for illustrative purpose, "a compound of Formula (I) or a pharmaceutically acceptable salt, solvate or N-oxide thereof" encompasses a pharmaceutically acceptable salt of a compound of Formula (I) which is present as a solvate, or this phrase may include a mixture of a compound of Formula (I) and a salt of a compound of Formula (I).

It will be further appreciated that all crystalline forms, polymorphs and enantiomers of the compounds of the invention, or mixtures thereof, are contemplated to be within the scope of the present invention. Unless otherwise specified (for example when the absolute stereochemistry is shown), for compounds of the invention which possesses stereocentres and which can therefore form enantiomers, (for example, when $R^2$ represents hydroxy), the compound contains a 1:1 mixture of enantiomers, i.e. a racemic mixture of enantiomers. These may be separated using conventional techniques such as chiral HPLC.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of Formula (I) are intended for use in pharmaceutical compositions it will readily be understood that in particular embodiments they are provided in substantially pure form, for example at least 60% pure, more suitably at least 75% pure and particularly at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and more particularly from 10 to 59% of a compound of Formula (I) or pharmaceutically acceptable salt, solvate and/or N-oxide thereof.

Pharmaceutically acceptable salts of the compounds of Formula (I) include the acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. In one aspect of the invention, the salt of a compound of Formula (I) is the hydrochloride salt. In another aspect, the salt of a compound of Formula (I) is the dihydrochloride salt. Compounds of Formula (I) may also be prepared as the N-oxide. The invention extends to all such salts, solvates and/or N-oxides.

COMPOUND PREPARATION

The general procedures used to synthesise the compounds of Formula (I), are described in reaction Schemes 1-11 and are illustrated in the Examples.

Compounds of Formula (I), wherein $R^1$, $R^2$, $R^5$ and Ar are as defined for Formula (I), may be prepared by a reductive amination reaction between a compound of Formula (II), wherein $R^1$, $R^2$ and $R^5$ are as defined for Formula (I), or an acid salt of a compound of Formula (II) such as a hydrochloride salt, and an aldehyde of Formula (III), wherein Ar is as defined for Formula (I), according to Scheme 1. Compounds (II) are reacted with compounds (III) in the presence of a hydride donor such as $NaBH(AcO)_3$ or polymer-supported $NaBH_3CN$, optionally in the presence of a catalytic acid such as acetic acid or a base such as triethylamine, in the presence of a suitable solvent such as 1,2-dichloroethane, or THF, or a mixture of DCM and MeOH, to give compounds (I).

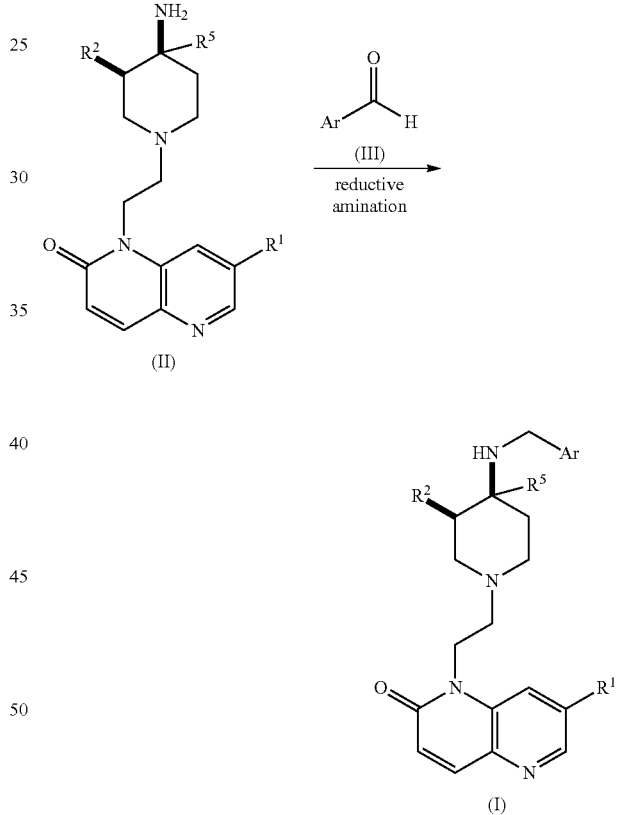

Scheme 1

Alternatively, compounds of Formula (I), wherein $R^1$, $R^5$ and Ar are as defined for Formula (I) and $R^2$ is hydrogen, may be prepared by an alkylation reaction between a compound of Formula (II), wherein $R^1$ is as defined for Formula (I) and $R^2$ is hydrogen, and an alkylating agent of Formula (IV), wherein Ar is as defined for Formula (I) and hal is a halo substituent, for example bromo, according to Scheme 2. Compounds (II) are reacted with compounds (IV) in the presence of a suitable base such as $K_2CO_3$ in a suitable solvent such as acetonitrile, to give compounds (I).

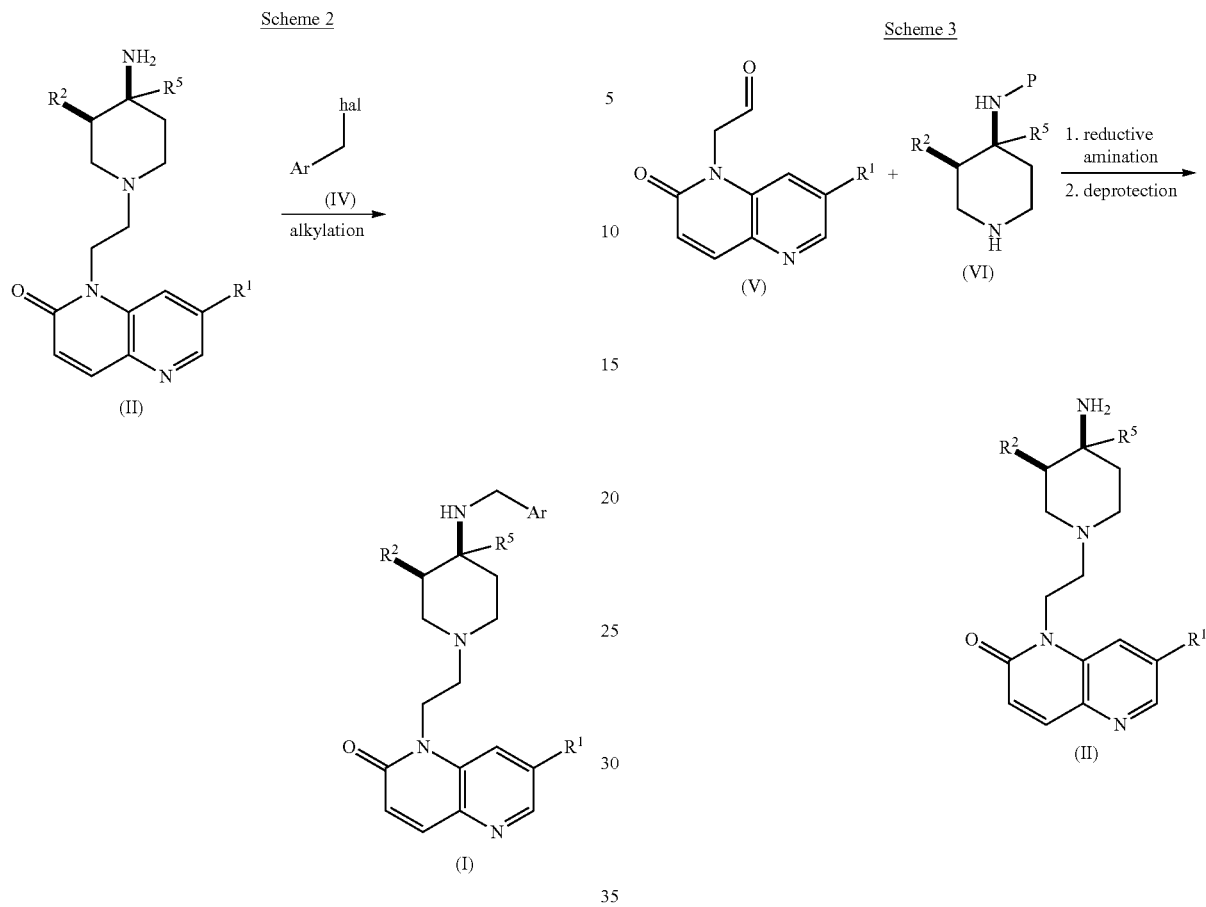

The acid salts of compounds of Formula (I), wherein $R^1$, $R^2$, $R^5$ and Ar are as defined for Formula (I), may be prepared by treating a solution of a compound of Formula (I) in a suitable solvent such as DCM with a suitable acid. For example, to make a hydrochloride salt of a compound of Formula (I), a solution of HCl in 1,4-dioxane or in MeOH may be employed. If a monohydrochloride salt of a compound of Formula (I) is required, for example one equivalent of HCl may be used. If a dihydrochloride salt of a compound of Formula (I) is required, an excess of HCl may be used.

Compounds of Formula (II), wherein $R^2$ is as defined for Formula (I) and $R^1$ is hydrogen; halo; or $C_{1-3}$alkoxy-, may be prepared by a reductive amination reaction between compounds of Formula (V), wherein $R^1$ is hydrogen; halo; or $C_{1-3}$alkoxy-, and compounds of Formula (VI), wherein $R^2$ and $R^5$ are as defined for Formula (I) and P is a nitrogen protecting group such as BOC, followed by a deprotection reaction, according to Scheme 3. Compounds (V) are reacted with compounds (VI) in the presence of a hydride donor such as $NaBH(AcO)_3$, in a suitable solvent such as $CHCl_3$ or DCM, or a mixture of either of these solvents with MeOH, followed by a deprotection reaction to remove the protecting group P. For Example, when the protecting group is BOC, this may be removed by treatment with a suitable acid such as HCl (for example a solution in 1,4-dioxane) in a suitable solvent such as DCM, to give the hydrochloride salt of compounds (II). If the free base of compound (II) is required, this may be followed by treatment with a suitable base such as aqueous NaOH with cooling, to give compounds (II).

Compounds of Formula (II), wherein $R^2$ is hydrogen and $R^1$ is $C_{1-3}$alkoxy-, may be prepared from a compound of Formula (II), wherein $R^2$ is hydrogen and $R^1$ is fluoro, as shown in Scheme 4. The fluoro compound of Formula (II) may be treated with a suitable base such as NaH in a suitable solvent such as a mixture of 1,4-dioxane and the appropriate alcohol $C_{1-3}$alkylOH, in the presence of heat, for example in a microwave oven.

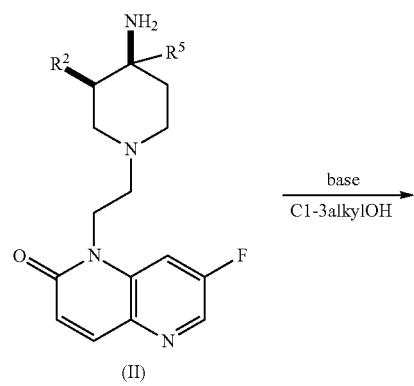

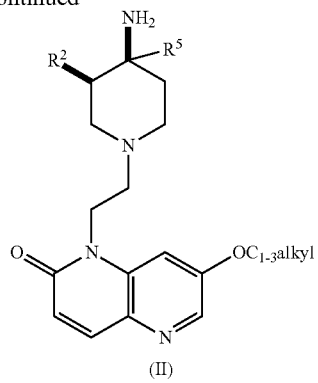

(II)

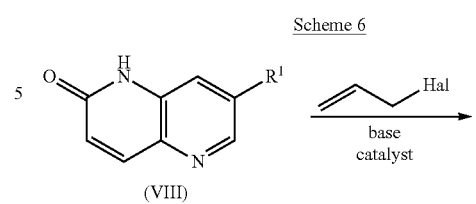

Compounds of Formula (VI), wherein $R^2$ is hydrogen are commercially available (for example from Aldrich). Compounds of Formula (VI), wherein $R^2$ is hydroxy and protecting group P is for example BOC, may be prepared according to the procedure given in WO2004058144, Example 5(c), cis-(3-hydroxy-piperidin-4-yl)-carbamic acid tert-butyl ester Enantiomer 1.

Compounds of Formula (V), wherein $R^1$ is hydrogen; halo; or $C_{1-3}$alkoxy-, may be prepared by oxidation of a compound of Formula (VII), wherein $R^1$ is hydrogen; halo; or $C_{1-3}$alkoxy-, according to Scheme 5. Compounds (VII) are treated with a suitable oxidising agent such as a mixture of sodium periodate and osmium tetroxide, in a suitable solvent such as a mixture of 1,4-dioxane and water, to give compounds (V).

Compounds of Formula (VIII), wherein $R^1$ is hydrogen; halo; or $C_{1-3}$alkoxy-, may be prepared by a hydrolysis reaction of compounds of Formula (IX), wherein $R^1$ is hydrogen; halo; or $C_{1-3}$alkoxy-, according to Scheme 7. Compounds (IX) may be treated with an acid, such as aqueous HCl, at elevated temperature, for example 90-110° C., to give compounds (VIII).

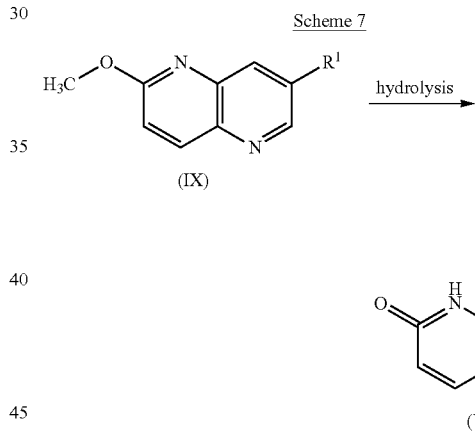

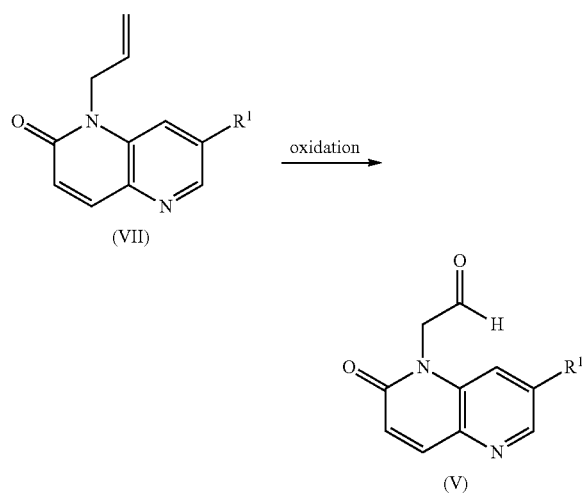

Compounds of Formula (VII), wherein $R^1$ is hydrogen; halo; or $C_{1-3}$alkoxy-, may be prepared by N-alkylation of compounds of Formula (VIII), wherein $R^1$ is hydrogen; halo; or $C_{1-3}$alkoxy-, according to Scheme 6. Compounds (VIII) are treated with a compound of Formula $CH_2$=CH—$CH_2$-hal, wherein hal is a halo substituent, for example with allyl bromide, in the presence of a suitable base such as NaH and optionally a catalyst such as LiBr, in a suitable solvent such as a mixture of DME and DMF, at elevated temperature, for example from 50-75° C., to give compounds (VII).

Compounds of Formula (IX), wherein $R^1$ is hydrogen; halo; or $C_{1-3}$alkoxy-, may be prepared from compounds of Formula (X), wherein $R^1$ is hydrogen; halo; or $C_{1-3}$alkoxy-, and halo is chloro or bromo, for example bromo, according to Scheme 8. Compounds (X) are subjected to hydrogenation in the presence of a suitable catalyst such as palladium on charcoal, in the presence of a suitable base such as $NaHCO_3$, to give compounds (IX).

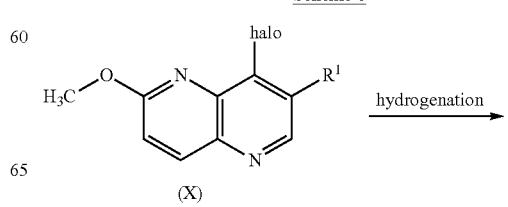

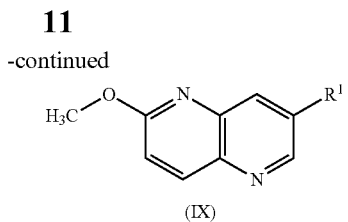

(IX)

Compounds of Formula (X), wherein R¹ is hydrogen or halo, may be prepared from compounds of Formula (XI), wherein R¹ is hydrogen or halo, according to Scheme 9. Compounds (XI) are treated with a source of chloride or bromide, such as PBr₃, in a suitable solvent such as DMF, to give compounds (X).

Scheme 9

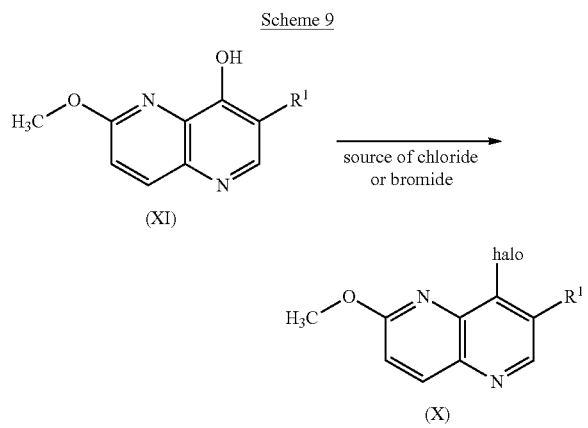

The compound of Formula (XI), wherein R¹ is hydrogen, may be prepared according to the procedure provided in WO2007016610, preparation 2 (a).

Compounds of Formula (XI), wherein R¹ is halo, for example fluoro, may be prepared according to the synthesis in Scheme 10.

Scheme 10

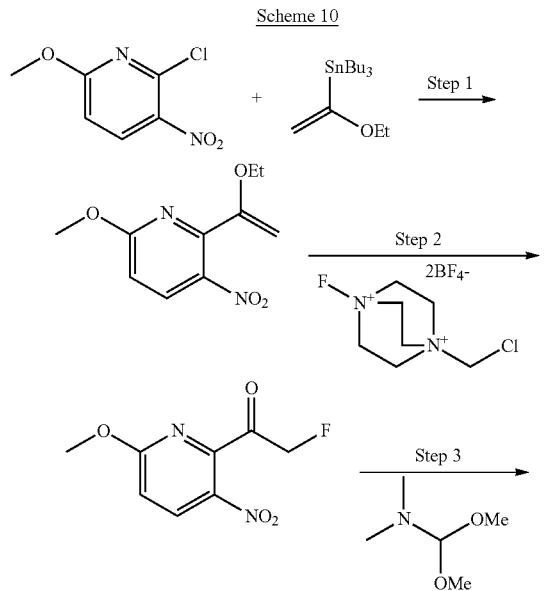

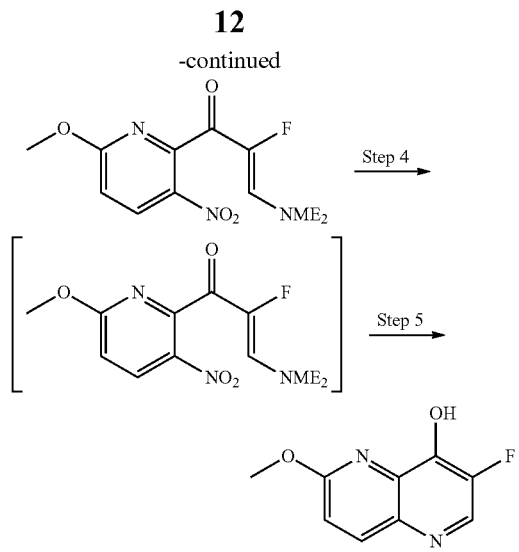

Step 1: Catalyst such as PdCl₂(PPh₃)₂; Solvent such as CH₃CN; Heating at 40-65° C.
Step 2: Solvent such as a mixture of CH₃CN and H₂O.
Step 3: Solvent such as PhCH₃; Heating such as 50° C.
Step 4: Hydrogenation in the presence of a catalyst such as palladium on charcoal; Solvent such as DMF; Heating at 45-50° C.
Step 5: Acid such as aqueous 6N HCl; Solvent such as DMF.

Compounds of Formula (X), wherein R¹ is $C_{1-3}$alkoxy-, may be prepared from compounds of Formula (X), wherein R¹ is halo, for example fluoro, according to Scheme 11. Compounds (X), wherein R¹ is fluoro, are treated with an appropriate base such as $NaOC_{1-3}$alkyl, for example NaOMe, in the appropriate alcohol solvent ($C_{1-3}$alkylOH), for example methanol, at elevated temperature, for example 40-65° C.

Scheme 11

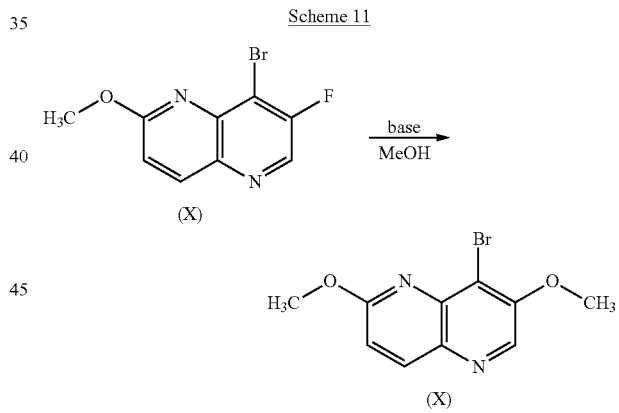

Compounds of Formula (I) in which R⁵ is methyl may be prepared using Scheme 12 below. Although illustrated with a group Ar which is pyridyl, the same methodology is expected to be useful for other groups Ar.

Scheme 12

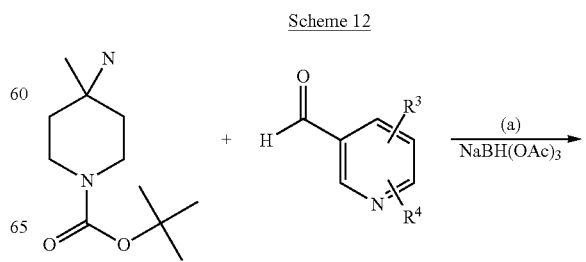

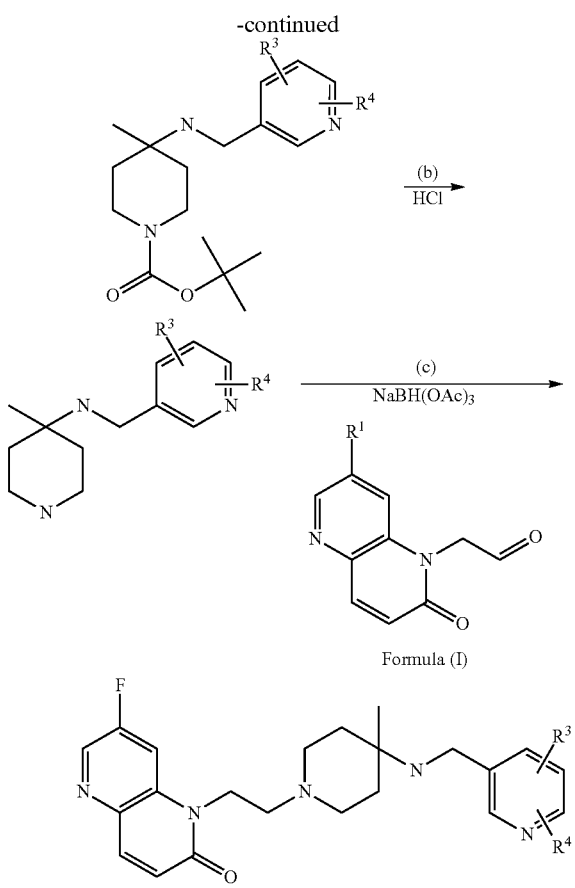

Formula (I)

Step 12(a) may be performed at room temperature in dichloromethane. Step 12(b) may be performed in dichloromethane at room temperature. Step 12(c) may be performed at room temperature in dichloromethane.

Compounds of Formula (III) and (IV), for example aldehyde compounds, are either known, are commercially available, or their method of manufacture will be apparent to those skilled in the art.

Those skilled in the art will appreciate that in the preparation of the compound of Formula (I), it may be necessary and/or desirable to protect one or more sensitive groups in the molecule or the appropriate intermediate to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl or aralkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

It will be readily apparent to those skilled in the art that other compounds of Formula (I) may be prepared using methods analogous to those outlined above, or by reference to the experimental procedures detailed in the Examples provided herein. Further details for the preparation of compounds of Formula (I) are found in the Examples.

COMPOSITIONS AND FORMULATIONS

The compounds of the invention may be formulated for administration in any convenient way for use in human or veterinary medicine, by analogy with formulation of antibacterials, or formulation of other antitubercular agents.

The compounds of the invention will normally, but not necessarily, be formulated into pharmaceutical compositions prior to administration to a patient. In one aspect, the invention is directed to a pharmaceutical composition comprising a compound of Formula (I), or a pharmaceutically acceptable salt, solvate or N-oxide thereof. In another aspect the invention is directed to a pharmaceutical composition comprising a compound of Formula (I), or a pharmaceutically acceptable salt, solvate or N-oxide thereof, and one or more pharmaceutically acceptable carriers, excipients or diluents. The carrier, excipient or diluent must be "acceptable" in the sense of being compatible with the other ingredients of the formulation and not deleterious to the recipient thereof.

The pharmaceutical compositions of the invention include those in a form adapted for oral, or parenteral use and may be used for the treatment of tuberculosis in mammals including humans.

The pharmaceutical compositions of the invention include those in a form adapted for oral, topical or parenteral use and may be used for the treatment of bacterial infections in mammals including humans.

The composition may be formulated for administration by any convenient route. For the treatment of tuberculosis, the compositions may be in the form of tablets, capsules, powders, granules, lozenges, aerosols or liquid preparations, such as oral or sterile parenteral solutions or suspensions. For the treatment of bacterial infections the compositions may be in the form of tablets, capsules, powders, granules, lozenges, creams, aerosols or liquid preparations, such as oral or sterile parenteral solutions or suspensions.

For the treatment of bacterial infections the topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

In one aspect of the invention, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-1000 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 30 mg/kg per day.

The compound of Formula (I), or a pharmaceutically acceptable pharmaceutically acceptable salt, solvate or N-oxide thereof, may be the sole therapeutic agent in the compositions of the invention, or it may be present in the formulation in combination with one or more additional therapeutic agents. The invention thus provides, in a further aspect, a combination comprising a compound of Formula (I), or a pharmaceutically acceptable salt, solvate or N-oxide thereof together with one or more additional therapeutic agents.

The one or more additional therapeutic agent is, for example, an agent useful for the treatment of tuberculosis in a mammal. Examples of such therapeutic agents include isoniazid, ethambutol, rifampin, pirazinamide, streptomycin, capreomycin, ciprofloxacin and clofazimine.

When a compound of Formula (I), or a pharmaceutically acceptable pharmaceutically acceptable salt, solvate or N-oxide thereof is used in combination with one or more additional therapeutic agents, the dose of the compound or agent may differ from that when the compound or agent is used alone. Appropriate doses will be readily appreciated by those skilled in the art. It will be appreciated that the amount of a compound of the invention and the one or more additional therapeutic agents required for use in treatment will vary with the nature of the condition being treated and the age and the condition of the patient and will be ultimately at the discretion of the attendant physician or veterinarian.

The combinations may conveniently be presented for use in the form of a pharmaceutical formulation. In a further aspect of the present invention there is provided a pharmaceutical combination comprising a compound of Formula (I), or a pharmaceutically acceptable salt, solvate or N-oxide thereof, together with one or more additional therapeutic agents, and one or more pharmaceutically acceptable carriers, excipients or diluents. The individual components of such combinations may be administered either sequentially or simultaneously in separate or combined pharmaceutical formulations by any convenient route.

When administration is sequential, either the compound of the present invention or one or more additional therapeutic agent may be administered first. When administration is simultaneous, the combination may be administered either in the same or different pharmaceutical composition. When combined in the same formulation it will be appreciated that the compound and agents must be stable and compatible with each other and the other components of the formulation. When formulated separately they may be provided in any convenient formulation, conveniently in such manner as are known for such compounds in the art.

ABBREVIATIONS

In describing the invention, chemical elements are identified in accordance with the Periodic Table of the Elements. Abbreviations and symbols utilized herein are in accordance with the common usage of such abbreviations and symbols by those skilled in the chemical arts. The following abbreviations are used herein:

EtOAc ethyl acetate
AcOH acetic acid
Ac2O acetic anhydride
BOC N-tert-butoxycarbonyl
BOC anhydride di-tert-butyl dicarbonate
Celite® a filter aid composed of acid-washed diatomaceous silica, (a trademark of Manville Corp., Denver, Colo.)
DME dimethoxyethane
DCM dichloromethane
DIBAL-H diisobutyl aluminium hydride
DMF dimethylformamide
DMSO-d6 deuterated dimethylsulfoxide
DMSO dimethylsulfoxide
ES MS Electrospray mass spectrometry
EtOH ethanol
h hours
HPLC high performance liquid chromatography
NaBH(OAc)$_3$ sodium triacetoxyborohydride
NMR Nuclear Magnetic Resonance spectroscopy
t-BuOMe methyl t-butyl ether
TFA trifluoroacetic acid
THF tetrahydrofuran
uv ultraviolet
LCMS Liquid chromatography mass spectroscopy
mCPBA meta-chloro perbenzoic acid
MeOH methanol

EXAMPLES

The following Examples illustrate the invention. These Examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made. References to preparations carried out in a similar manner to, or by the general method of, other preparations, may encompass variations in routine parameters such as time, temperature, workup conditions, minor changes in reagent amounts etc.

Proton nuclear magnetic resonance ($^1$H NMR) spectra were recorded, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. Mass spectra were obtained using electrospray (ES) ionization techniques. All temperatures are reported in degrees centigrade.

Reactions involving metal hydrides including lithium hydride, lithium aluminium hydride, di-isobutylaluminium hydride, sodium hydride, sodium borohydride and sodium triacetoxyborohydride are carried out under argon unless otherwise specified.

PREPARATION OF INTERMEDIATES

Intermediate 1

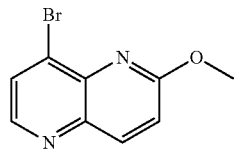

8-Bromo-2-(methyloxy)-1,5-naphthyridine 6-(Methyloxy)-1,5-naphthyridin-4-ol (21.5 g) (for a synthesis see WO2007016610 Preparation 2 (a)) was stirred in DMF (150 ml) at 0° C. under $N_2$, and phosphorous tribromide (13.5 ml) was added slowly. The mixture was allowed to warm to room temperature and stirred for 90 minutes. $H_2O$ (375 ml) was added and the pH was adjusted to pH 7 by addition of solid $Na_2CO_3$. The solid was isolated by filtration with suction, dried on the sinter with suction for 2 h then dried under vacuum at 45° C. to give the desired compound (26.0 g, 90%). $^1$H-NMR (δ, ppm, DMSO-$d_6$): 8.59 (d, 1H), 8.30 (d, 1H), 8.08 (d, 1H), 7.33 (d, 1H), 4.06 (s, 3H).

Intermediate 2

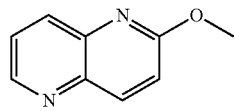

2-(Methyloxy)-1,5-naphthyridine

To a mixture of Intermediate 1 (25.5 g) in $CH_2Cl_2$ (200 ml) and EtOH (200 ml) was added $NaHCO_3$ (20 g) and 5% wet palladium on carbon (4 g). The resulting suspension was hydrogenated at 1.5 bar for 21 h. The mixture was filtered with suction through celite and the solids were washed with $CH_2Cl_2$/EtOH 1:1 (2000 ml). The combined filtrate plus washings were concentrated under reduced pressure and then treated with $CH_2Cl_2$/$H_2O$ 2:1 (1600 ml). The organic phase was separated, dried over $MgSO_4$, filtered and evaporated under reduced pressure to give the desired compound (15.8 g, 92%). [ES MS] m/z 161 (MH$^+$).

Intermediate 3

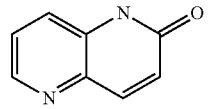

1,5-Naphthyridin-2(1H)-one

Intermediate 2 (15.8 g) was stirred in 6N HCl (100 ml) at 110° C. for 2 h. The mixture was cooled at 0° C. and the pH was adjusted to 6-7 with solid NaOH. The precipitated solid was isolated by filtration with suction, dried on the sinter with suction for 2 h, and dried in a vacuum at 45° C. to give the desired (14.4 g, 98%). [ES MS] m/z 147 (MH$^+$).

Intermediate 4

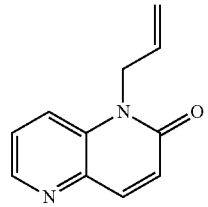

1-(2-Propen-1-yl)-1,5-naphthyridin-2(1H)-one

To a suspension of Intermediate 3 (5.9 g) in dry DME (180 ml) and dry DMF (45 ml) at 0° C. under argon was added in portions NaH (60% w:w dispersion in mineral oil, 3.2 g). After stirring for 45 minutes, the mixture was treated with lithium bromide (8.8 g) and the suspension was allowed to warm to room temperature. After stirring for 45 minutes, the mixture was treated with allyl bromide (7 ml) and then stirred at 65° C. for 3 h. The mixture was cooled to room temperature and concentrated under reduced pressure, then t-BuOMe (300 ml) was added and the mixture was then washed with 1N $NH_4Cl$ (200 ml).

The combined aqueous phases were extracted with t-BuOMe (2×100 ml). The organic phases were combined, washed with brine (200 ml), dried over $Na_2SO_4$, filtered and evaporated under reduced pressure. The residue was purified by column chromatography on silica gel using a EtOAc and hexane gradient (50-75%) to give the desired product (4.29 g, 57%). To obtain an additional amount of the desired compound, the combined aqueous phases were extracted exhaustively with $CH_2Cl_2$. Then, the organic extracts were combined, dried over $MgSO_4$, filtered and evaporated under reduced pressure. The residue was purified by column chromatography on silica gel using a EtOAc and hexane gradient (50-75%) to give the desired product (1.5 g, 20%). [ES MS] m/z 187 (MH+).

Intermediate 5

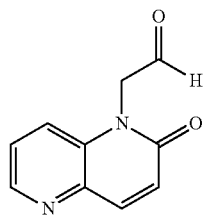

(2-Oxo-1,5-naphthyridin-1(2H)-yl)acetaldehyde (mixture with the methyl hemiacetal)

To a solution of Intermediate 4 (5.2 g) in 1,4-dioxane (100 ml) and H$_2$O (50 ml) was added consecutively sodium periodate (13.8 g) and osmium tetroxide (4 g of Supported OsO$_4$). The mixture was stirred at room temperature for 24 h. Additional amount of sodium periodate (1.4 g) and osmium tetroxide (500 mg) was added and the mixture was stirred another 72 h. The mixture was filtered and the solid washed with H$_2$O (250 ml) and THF (125 ml). The combined filtrate plus washings were extracted with CH$_2$Cl$_2$/MeOH (525/125; 375/125 and 375/125 ml). The organic extracts were combined, dried over Na$_2$SO$_4$, filtered and evaporated under reduced pressure to give the desired product (5.4 g, 90%). $^1$H-NMR (δ, ppm, CDCl$_3$): 9.75 (s, ½H), 8.59-8.55 (m, 1H), 8.03-7.85 (m, 2H), 7.50-7.30 (m, 2H), 6.98 (d, 1H), 5.15-4.25 (m, 5H), 3.70 (s, 3H), 3.49 (s, ½H), 3.42-3.30 (m, 1H).

Intermediate 6

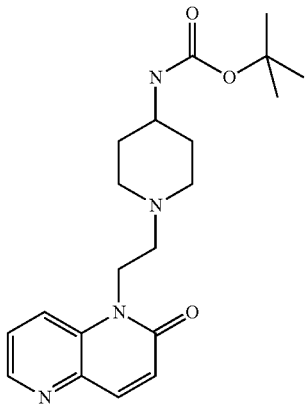

1,1-Dimethylethyl {1-[2-(2-oxo-1,5-naphthyridin-1(2H)-yl)ethyl]-4-piperidinyl}carbamate To a mixture of Intermediate 5 (10.2 g) in CH$_2$Cl$_2$ (350 ml) and MeOH (20 ml) was added 1,1-dimethylethyl-4-piperidinylcarbamate (10.8 g, from Aldrich). After stirring for 1 h, sodium triacetoxyborohydride (34.4 g) was added. The reaction was stirred for 3 h before addition of H$_2$O (200 ml) and saturated NaHCO$_3$ (400 ml). The reaction was extracted with CH$_2$Cl$_2$/MeOH (500/75, 450/50 and 450/50 ml). The combined organic phases were dried over Na$_2$SO$_4$, evaporated and the residue was purified by chromatography on silica gel using a CH$_2$Cl$_2$ and MeOH gradient to provide the desired compound (12.7 g, 63%). [ES MS] m/z 373 (MH+).

Intermediate 7

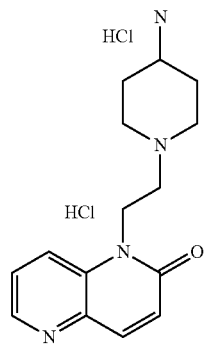

1-[2-(4-Amino-1-piperidinyl)ethyl]-1,5-naphthyridin-2(1H)-one dihydrochloride

To a solution of Intermediate 6 (7.2 g) in CH$_2$Cl$_2$ (90 ml) was added HCl (4M solution in 1,4-dioxan, 35 ml). After stirring for 20 h, the obtained solid was filtered, washed with CH$_2$Cl$_2$ and dried to give 6.8 g of the title compound. $^1$H-NMR (δ, ppm, D$_2$O): 8.52 (d, 1H), 8.22 (d, 1H), 7.99 (d, 1H), 7.82-7.78 (m, 1H), 6.99 (d, 1H), 4.66-4.60 (m), 3.79-3.72 (m, 2H), 3.48-3.42 (m, 3H), 3.14-3.03 (m, 2H), 2.23-2.15 (m, 2H), 1.87-1.76 (m, 2H).

Intermediate 8

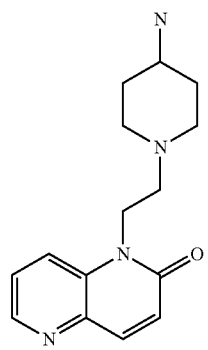

1-[2-(4-Amino-1-piperidinyl)ethyl]-1,5-naphthyridin-2(1H)-one

To a solution of Intermediate 7 (2 g) in H$_2$O (20 ml) at 0° C. was added aqueous 1N NaOH until pH 11. The reaction was then extracted with CH$_2$Cl$_2$/MeOH 95:5 (50 ml). The organic phase was dried over Na$_2$SO$_4$ and evaporated to give the desired compound (387 mg). The aqueous phase was evaporated and the residue was treated with CH$_2$Cl$_2$ (25 ml) and the mixture was stirred for 1 h. Then it was filtered and the solvent was evaporated to give an additional amount of the title compound (1.0 g). ¹H-NMR (δ, ppm, CDCl₃): 8.55 (d, 1H), 7.90 (d, 1H), 7.77 (d, 1H), 7.48-7.44 (m, 1H), 6.91 (d, 1H), 4.38 (t, 2H), 2.99-2.94 (m, 2H), 2.73-2.62 (m, 3H), 2.18 (dt, 2H), 1.87-1.76 (m, 2H); 1.43-1.30 (m, 2H), 1.25-1.13 (m, 2H).

Intermediate 9

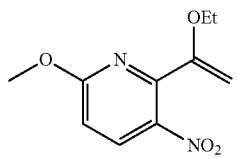

2-[1-(Ethyloxy)ethenyl]-6-(methyloxy)-3-nitropyridine

To a suspension of 2-chloro-6-methoxy-3-nitropyridine (600 g) and PdCl₂(PPh₃)₂ (33.5 g) in acetonitrile (4200 ml) at 65° C. under N₂ was added dropwise over 2 h (1-ethoxyvinyl)-tributyl-stannane (1182 ml). The resulting suspension was stirred at 65° C. for 4 h then left to cool to room temperature overnight. The reaction mixture was quenched with 10% KF aqueous solution (3600 ml) with vigorous stirring and stirred for 1 h. The resulting solid was removed by vacuum filtration and washed with acetonitrile (7×1000 ml). The layers were separated and the organic layer was evaporated to 3000 ml. This was filtered through Whatman, GF/B glass microfibre filter paper and the small amount of brown solid removed was washed with MeCN (1800 ml). EtOAc (3600 ml) was added and the volume reduced to 1800 ml. Cyclohexane (3600 ml) was added and the volume reduced to 3000 ml. Cyclohexane (2400 ml) and silica gel (600 g, 1 wt) were added and allowed to stir at room temperature for 1.5 h. The solid was removed by vacuum filtration and washed with EtOAc/cyclohexane, 1:8 (4200 ml). The filtrate was reduced to 1800 ml. Cyclohexane (2400 ml) was added and the volume reduced to 1800 ml. Cyclohexane (3600 ml) and EtOAc (600 ml) and silica gel (600 g, 1 wt) were added and stirred for 1.5 h. The solid was removed by vacuum filtration and washed with EtOAc/cyclohexane 1:8 (4200 ml). The solvents were evaporated to dryness. MeCN (2000 ml) was added and evaporated to give an orange coloured oil.

Intermediate 10

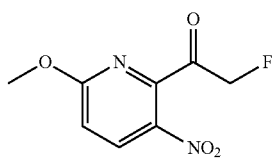

2-Fluoro-1-[6-(methyloxy)-3-nitro-2-pyridinyl]ethanone

To a suspension of Selectfluor (1286.4 g) in acetonitrile (2060 ml) and H₂O (820 ml) was added dropwise over 1.5 h Intermediate 9 in acetonitrile (1416 ml), maintaining the temperature <15° C. using an ice/water bath. The resulting solution was stirred at room temperature overnight. The reaction mixture was quenched with saturated aqueous NaHCO₃ (2140 ml) and stirred for 30 minutes. The volume was reduced by rotary evaporation to 3250 ml. To the resulting yellow suspension was added EtOAc (4400 ml) and H₂O (720 ml) and allowed to stir for 15 minutes. The layers were separated and the aqueous extracted with EtOAc (2×1000 ml). The organic layers were combined and washed with H₂O (1000 ml) and saturated NaCl (1000 ml). The organic layer was dried over MgSO₄ (400 g), filtered and evaporated. Acetonitrile (1000 ml) was added and evaporated to give an orange oil which slowly solidified on standing.

Intermediate 11

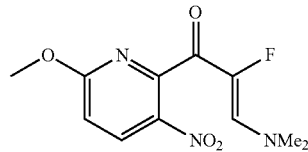

(2Z)-3-(Dimethylamino)-2-fluoro-1-[6-(methyloxy)-3-nitro-2-pyridinyl]-2-propen-1-one To a solution of Intermediate 10 (657.0 g) in toluene (2700 ml) under N₂ was added N,N-dimethylformamide dimethylacetal (1550 ml). The reaction mixture was heated at 50° C. for 4 h. Cyclohexane (2000 ml) was added and the reaction mixture was cooled slowly over 1 h, then to <5° C. using an ice/water bath. The precipitated solid was collected by vacuum filtration and washed with EtOAc/cyclohexane, 1:1 (3×1000 ml). The yellow solid was dried in the oven, under vacuum at 40° C. overnight.

Intermediate 12

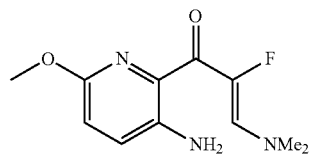

(2Z)-1-[3-Amino-6-(methyloxy)-2-Pyridinyl]-3-(dimethylamino)-2-fluoro-2-propen-1-one To a mixture of Intermediate 11 (1146.7 g) in DMF (10500 ml) was added 5% wet palladium on carbon (274.4 g) in DMF (1000 ml). The resulting suspension was hydrogenated at 1.0 bar for 3 h, maintaining the temperature between 45-50° C. The reaction mixture was warmed to 60° C. DMF (1800 ml) was warmed to 50° C. and charged to the pressurised filter. The hot reaction mixture was nitrogen transferred through the pressurised filter, at 1.0 bar, to remove the catalyst. The vessel was rinsed out with hot DMF (2×1500 ml). The product was not isolated and used directly in the next step.

Intermediate 13

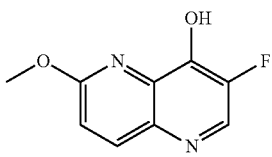

3-Fluoro-6-(methyloxy)-1,5-naphthyridin-4-ol

To a solution of Intermediate 12 in DMF at 0° C. was added dropwise aqueous 6N HCl (184 ml). The reaction was allowed to warm to room temperature and stirred overnight.

The volume of the reaction mixture was reduced to ~2000 ml by rotary evaporation at 50° C. and the yellow suspension was cooled to 10° C. using an ice/water bath. H$_2$O (4000 ml) was added slowly over 30 minutes. The reaction mixture was stirred vigorously for 1 h. The precipitated solid was collected by vacuum filtration and washed with H$_2$O (3000 ml) then EtOAc/cyclohexane, 1:1 (3×2000 ml). The pale brown solid was dried in the oven, under vacuum at 50° C. for 4 days.

Intermediate 14

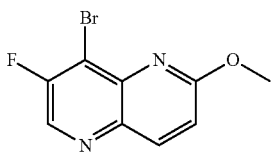

8-Bromo-7-fluoro-2-(methyloxy)-1,5-naphthyridine

This was prepared from Intermediate 13 (15.8 g) using a procedure analogous to that described for Intermediate 1 to give 19.6 g (93%) of the title compound. $^1$H-NMR (δ, ppm, DMSO-d$_6$): 8.86 (s, 1H), 8.34 (d, 1H), 7.31 (d, 1H), 4.08 (s, 3H).

Intermediate 15

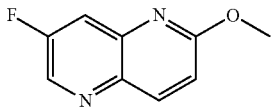

7-Fluoro-2-(methyloxy)-1,5-naphthyridine

This was prepared from Intermediate 14 (12.7 g) using a procedure analogous to that procedure described for Intermediate 2 to give 8.3 g (94%) of the title compound. $^1$H-NMR (δ, ppm, CDCl$_3$): 8.67 (d, 1H), 8.18 (d, 1H), 7.81-7.76 (m, 1H), 7.07 (d, 1H), 4.08 (s, 3H).

Intermediate 16

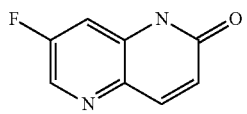

7-Fluoro-1,5-naphthyridin-2(1H)-one

This was prepared from Intermediate 15 (6.4 g) using a procedure analogous to that described for Intermediate 3 to give 5.7 g (95%) of the title compound. [ES MS] m/z 279 (MH$^+$).

Intermediate 17

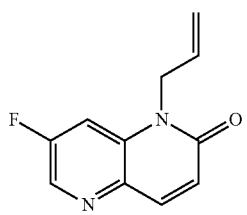

7-Fluoro-1-(2-propen-1-yl)-1,5-naphthyridin-2(1H)-one

This was prepared from Intermediate 16 (5.0 g) using a procedure analogous to that described for Intermediate 4 to give 5.4 g (88%) of the title compound. [ES MS] m/z 205 (MH$^+$).

Intermediate 18

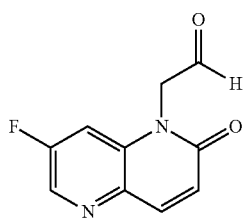

7-Fluoro-(2-oxo-1,5-naphthyridin-1(2H)-yl)acetaldehyde (mixture with the methyl hemiacetal)

This was prepared from Intermediate 17 (5.4 g) using a procedure analogous to that described for Intermediate 5 to give 5.8 g of the title compound. $^1$H-NMR (δ, ppm, CDCl$_3$):

9.77 (s, ½H), 8.45 (bs, 1H), 7.97 (d, 1H), 7.59 (d, ½H), 7.06 (d, 1H), 6.92 (d, 1H), 5.05-4.95 (m, 2H), 4.45-4.30 (m, 1H), 3.49 (s, ⅝H), 3.42 (s, ⅝H).

Intermediate 19

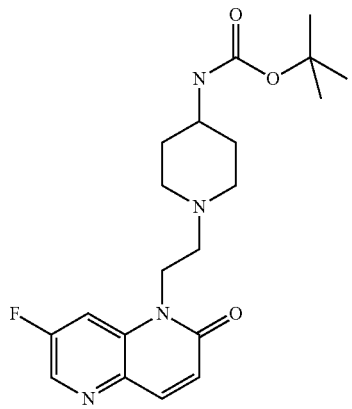

1,1-Dimethylethyl {1-[2-(7-fluoro-2-oxo-1,5-naph-thyridin-1(2H)-yl)ethyl]-4-piperidinyl}carbamate This was prepared from Intermediate 18 (5.8 g) using a procedure analogous to that described for Intermediate 6 to give 7.2 g (66%) of the title compound. [ES MS] m/z 391 (MH+).

Intermediate 20

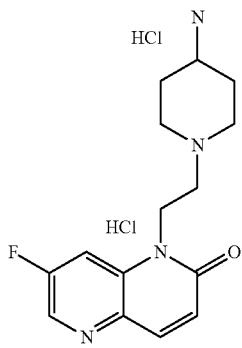

1-[2-(4-amino-1-piperidinyl)ethyl]-7-fluoro-1,5-naphthyridin-2(1H)-one dihydrochloride This was prepared from Intermediate 19 (12.7 g) using a procedure analogous to that described for Intermediate 7 to give 13.5 g of the title compound. $^1$H-NMR (δ, ppm, D$_2$O): 8.41 (s, 1H), 7.94 (d, 1H), 7.80 (d, 1H), 6.83 (d, 1H), 4.70- 4.55 (m), 3.85-3.75 (m, 2H), 3.46 (t, 2H), 3.15-3.05 (m, 2H), 2.25 (bd, 2H), 1.90-1.75 (m, 2H).

Intermediate 21

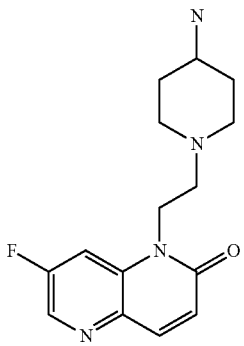

1-[2-(4-Amino-1-piperidinyl)ethyl]-7-fluoro-1,5-naphthyridin-2(1H)-one

To a solution of Intermediate 20 (13.5 g) in H$_2$O (110 ml) at 0° C. was added aqueous 2N NaOH until pH 11. The reaction was then extracted with CH$_2$Cl$_2$/MeOH 95:5 (120 ml). The organic phase was dried over Na$_2$SO$_4$ and evaporated to give the desired compound (760 mg). The aqueous phase was evaporated and the residue was treated with CH$_2$Cl$_2$/MeOH 95:5 (120 ml) and the mixture was stirred for 1 h. Then it was filtered and the solvent was evaporated to give an additional amount of the title compound (8.0 g). $^1$H-NMR (δ, ppm, DMSO-d$_6$): 8.54 (d, 1H), 8.01 (d, 1H), 7.92 (d, 1H), 4.29 (t, 2H), 3.65-3.15 (m, 4H), 3.35 (d, 2H), 2.80-2.70 (m, 1H), 2.53-2.48 (m), 2.01 (t, 2H), 1.72 (d, 2H), 1.35-1.20 (m, 2H).

Intermediate 22

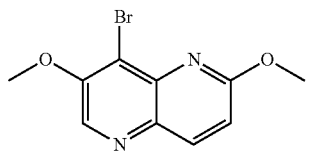

8-Bromo-2,7-bis(methyloxy)-1,5-naphthyridine

To a solution of Intermediate 14 (62.5 g) in dry MeOH (600 ml) under N$_2$ was added NaMeO (25% wt solution in MeOH, 525 ml). The mixture was stirred at 60° C. for 2 h and then, was cooled to room temperature. Brine (800 ml), H$_2$O (800 ml) and CH$_2$Cl$_2$ (1 L) were added. The mixture was stirred and filtered with suction. The organic phase was separated and the aqueous phase was extracted with more CH$_2$Cl$_2$ (2×500 ml). The combined organic phases were dried over Na$_2$SO$_4$ and concentrated under reduced pressure to give the desired compound (60.1 g, 92%). ¹H-NMR (δ, ppm, CDCl₃): 8.54 (s, 1H), 8.15 (d, 1H), 7.03 (d, 1H), 4.15, 4.16 (s, 6H).

Intermediate 23

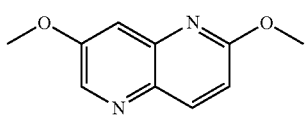

2,7-Bis(methyloxy)-1,5-naphthyridine

This was prepared from Intermediate 22 (15.0 g) using a procedure analogous to that described for Intermediate 2 to give 10.4 g (98%) of the title compound. ¹H-NMR (δ, ppm, CDCl₃): 8.52 (d, 1H), 8.14 (d, 1H), 7.46 (d, 1H), 6.96 (d, 1H), 4.07 (s, 3H), 3.96 (s, 3H).

Intermediate 24

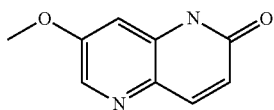

7-(Methyloxy)-1,5-naphthyridin-2(1H)-one

This was prepared from Intermediate 23 (39.7 g) using a procedure analogous to that described for Intermediate 3 to give 36.2 (98%) of the title compound. ¹H-NMR (δ, ppm, DMSO-d₆): 11.78 (bs, 1H), 8.19 (d, 1H), 7.84 (d, 1H), 7.12 (d, 1H), 6.52 (d, 1H), 3.86 (s, 3H).

Intermediate 25

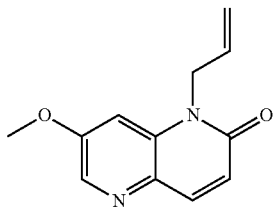

7-Methyloxy-1-(2-propen-1-yl)-1,5-naphthyridin-2(1H)-one

This was prepared from Intermediate 24 (15.0 g) using a procedure analogous to that described for Intermediate 4 to give 14.5 g (79%) of the title compound. ¹H-NMR (δ, ppm, CDCl₃): 8.27 (d, 1H), 7.87 (dd, 1H), 7.02 (d, 1H), 6.78 (d, 1H), 6.00-5.88 (m, 1H), 5.26 (d, 1H), 5.10 (d, 1H), 4.92-4.89 (m, 2H), 3.94 (s, 3H).

Intermediate 26

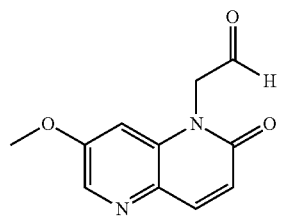

[7-(Methyloxy)-2-oxo-1,5-naphthyridin-1(2H)-yl]acetaldehyde

To a solution of Intermediate 25 (15.4 g) in 1,4-dioxane (250 ml) and H₂O (120 ml) was added consecutively sodium periodate (35 g) and osmium tetroxide (11.3 g of Supported OsO₄). The mixture was stirred at room temperature for 24 h. Additional amount of sodium periodate (3.5 g) and osmium tetroxide (1.2 g) was added and the mixture was stirred another 72 h. The mixture was filtered and the filtrate was extracted with CH₂Cl₂/MeOH 9:1 (300, 200 and 100 ml). The organic phases were combined, dried over Na₂SO₄, filtered and evaporated under reduced pressure to give the desired product (14.9 g, 95%). ¹H-NMR (δ, ppm, CDCl₃): 9.72 (s, 1H), 8.30 (d, 1H), 7.94 (d, 1H), 6.81 (d, 1H), 6.72 (bd, 1H), 5.11 (s, 2H), 3.93 (s, 3H).

Intermediate 27

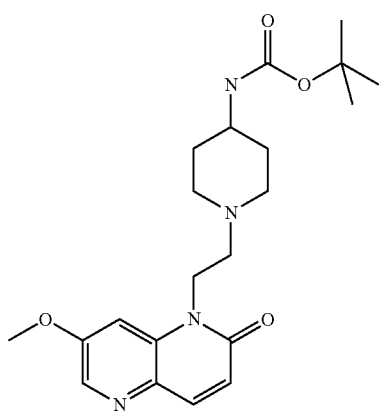

1,1-Dimethylethyl (1-{2-[7-(methyloxy)-2-oxo-1,5-naphthyridin-1(2H)-yl]ethyl}-4-piperidinyl)carbamate This was prepared from Intermediate 26 (12.8 g) using a procedure analogous to that described for Intermediate 6 to give 15.3 g (65%) of the title compound. ¹H-NMR (δ, ppm, CDCl₃): 8.27 (d, 1H), 7.83 (d, 1H), 7.17 (bs, 1H), 6.73 (d, 1H), 4.44 (bs, 1H), 4.35 (t, 2H), 3.97 (s, 3H), 3.47 (bs, 1H), 2.94 (bd, 2H), 2.64 (t, 2H), 2.26 (t, 2H), 1.95 (bd, 2H), 1.70 (bs, 2H), 1.44 (s, 9H).

Intermediate 28

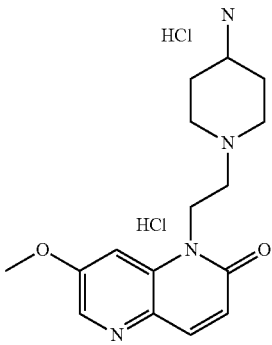

1-[2-(4-amino-1-piperidinyl)ethyl]-7-(methyloxy)-1,5-naphthyridin-2(1H)-one dihydrochloride This was prepared from Intermediate 27 (15.4 g) using a procedure analogous to that described for Intermediate 7.

Intermediate 29

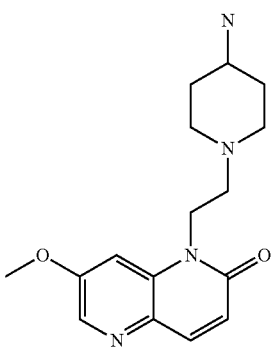

1-[2-(4-Amino-1-piperidinyl)ethyl]-7-methyloxy-1,5-naphthyridin-2(1H)-one

This was prepared from Intermediate 28 by the procedure described in Intermediate 21 to give 11.5 g (99%) of the title compound. $^1$H-NMR (δ, ppm, DMSO-d$_6$): 8.26 (d, 1H), 7.85 (d, 1H), 7.39 (d, 1H), 6.64 (d, 1H), 4.34 (d, 2H), 3.97 (s, 3H), 3.72 (bs, 2H), 2.92 (bd, 2H), 2.74-2.64 (m, 1H), 2.54-2.48 (m), 2.03 (t, 2H), 1.72 (bd, 2H), 1.35-1.24 (m, 2H).

Intermediate 30

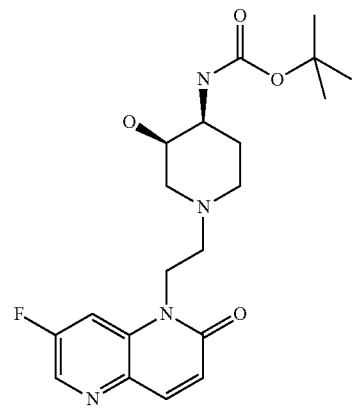

1,1-Dimethylethyl{(3R,4S)-1-[2-(7-fluoro-2-oxo-1,5-naphthyridin-1(2H)-yl)ethyl]-3-hydroxy-4-piperidinyl}carbamate Intermediate 18 (200 mg) and 1,1-dimethylethyl[(3R,4S)-3-hydroxy-4-piperidinyl]carbamate (182 mg) (for a synthesis see WO2004058144, Example 5(c), cis-(3-hydroxy-piperidin-4-yl)-carbamic acid tert-butyl ester Enantiomer 1) were stirred in CHCl$_3$ (10 ml) plus MeOH (0.5 ml) under argon for 2 h. Sodium triacetoxyborohydride (534 mg) was added in one portion and the mixture was stirred at room temperature overnight, then quenched by addition of saturated aqueous NaHCO$_3$ (20 ml) and extracted with 20% v:v MeOH in CH$_2$Cl$_2$ (3×200 ml). The organic extracts were combined, dried over anhydrous MgSO$_4$, filtered and evaporated under reduced pressure to give the crude product, which was purified by column chromatography on silica, eluted with 0-20% (2M ammonia in MeOH) in CH$_2$Cl$_2$. Appropriate fractions were combined and evaporated under reduced pressure to give title compound (247 mg) as an off-white foam. [ES MS] m/z 407 (MH$^+$).

Intermediate 31

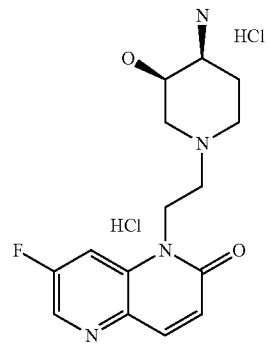

31

1-{2-[(3R,4S)-4-Amino-3-hydroxy-1-piperidinyl]ethyl}-7-fluoro-1,5-naphthyridin-2(1H)-one dihydrochloride Intermediate 30 (240 mg) was dissolved in CH$_2$Cl$_2$ (10 ml) and the solution was treated with 4M HCl in 1,4-dioxane (2 ml). Effervescence and formation of a precipitate was observed. After 2 h, the solvents were removed under reduced pressure and the residue was dried under reduced pressure overnight, to give 220 mg of the title compound as an off-white solid. [ES MS] m/z 307 (MH$^+$).

Intermediate 32

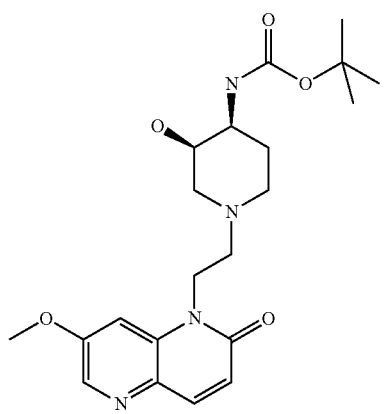

1,1-Dimethylethyl ((3R,4S)-3-hydroxy-1-{2-[7-(methyloxy)-2-oxo-1,5-naphthyridin-1(2H)-yl]ethyl}-4-piperidinyl)carbamate This was prepared from Intermediate 26 (200 mg) and 1,1-dimethylethyl[(3R,4S)-3-hydroxy-4-piperidinyl]carbamate (173 mg) (for a synthesis see WO2004058144, Example 5(c), cis-(3-hydroxy-piperidin-4-yl)-carbamic acid tert-butyl ester Enantiomer 1) using a procedure analogous to that described for Intermediate 30 to give 263 mg of the title compound. [ES MS] m/z 419 (MH$^+$).

Intermediate 33

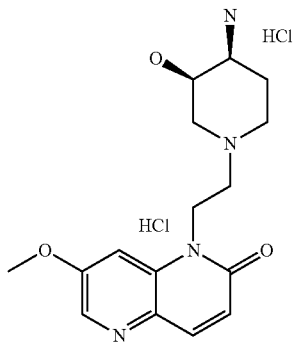

32

1-{2-[(3R,4S)-4-Amino-3-hydroxy-1-piperidinyl]ethyl}-7-(methyloxy)-1,5-naphthyridin-2(1H)-one dihydrochloride This was prepared from Intermediate 32 (258 mg) using a procedure analogous to that described for Intermediate 31 to give 223 mg of the title compound.

[ES MS] m/z 319 (MH$^+$).

Intermediate 34

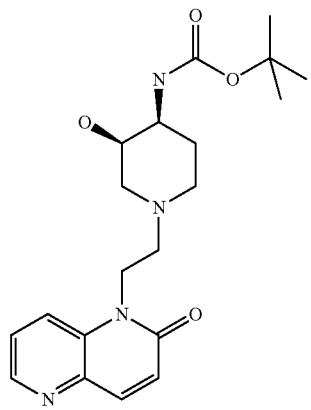

1,1-Dimethylethyl {(3R,4S)-3-hydroxy-1-[2-(2-oxo-1,5-naphthyridin-1(2H)-yl)ethyl]-4-piperidinyl}carbamate This was prepared from Intermediate 5 (639 mg) and 1,1-dimethylethyl[(3R,4S)-3-hydroxy-4-piperidinyl]carbamate (250 mg) (for a synthesis see WO2004058144, Example 5(c), cis-(3-hydroxy-piperidin-4-yl)-carbamic acid tert-butyl ester Enantiomer 1) using a procedure analogous to that described for Intermediate 30 to give 250 mg of the title compound.

Intermediate 35

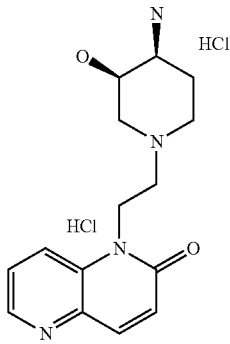

1-{2-[(3R,4S)-4-Amino-3-hydroxy-1-piperidinyl]ethyl}-1,5-naphthyridin-2(1H)-one dihydrochloride This was prepared from Intermediate 34 (250 mg) using a procedure analogous to that described for Intermediate 31 to give 250 mg of the title compound.

Intermediate 35b

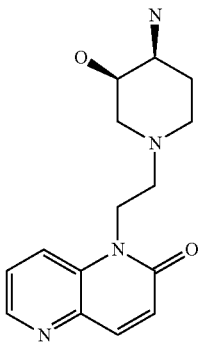

1-{2-[(3R,4S)-4-Amino-3-hydroxy-1-piperidinyl]ethyl}-1,5-naphthyridin-2(1H)-one

To a solution of Intermediate 35 in H$_2$O was added solid NaHCO$_3$ until pH 9. The reaction was then extracted with CH$_2$Cl$_2$/MeOH 9:1. The organic phase was dried over Na$_2$SO$_4$ and evaporated to give 28 mg of a yellow solid, which $^1$H-NMR was not consistent with the desired compound. The aqueous phase was evaporated and the residue was treated with CH$_2$Cl$_2$ and the mixture was stirred at room temperature. Then it was filtered and the solvent was evaporated to provide the title compound (free base) (45 mg). $^1$H-NMR (δ, ppm, CDCl$_3$): 8.56 (d, 1H), 7.92 (d, 1H), 7.71 (d, 1H), 7.47 (dd, 1H), 6.93 (d, 1H), 4.53-4.44 (m, 1H), 4.34-4.25 (m, 1H), 3.66 (bs, 1H), 3.09-3.06 (m, 1H), 2.85-2.81 (m, 1H), 2.72-2.65 (m, 3H), 2.34 (d, 1H), 2.26-2.17 (m, 1H), 1.64-1.57 (m, 5H).

Intermediate 36

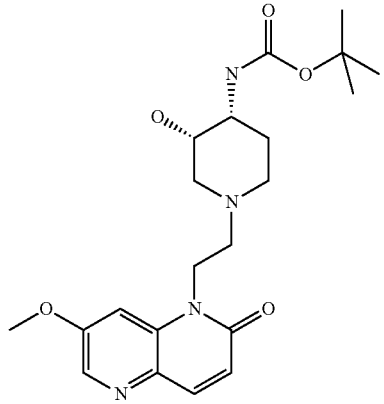

1,1-Dimethylethyl ((3S,4R)-3-hydroxy-1-{2-[7-(methyloxy)-2-oxo-1,5-naphthyridin-1(2H)-yl]ethyl}-4-piperidinyl)carbamate This was prepared from Intermediate 26 (200 mg) and 1,1-dimethylethyl[(3S,4R)-3-hydroxy-4-piperidinyl]carbamate (182 mg) (for a synthesis see WO2004058144, Example 5(c), cis-(3-hydroxy-piperidin-4-yl)-carbamic acid tert-butyl ester Enantiomer 2) using a procedure analogous to that described for Intermediate 30 to give 226 mg of the title compound. [ES MS] m/z 419 (MH$^+$).

Intermediate 37

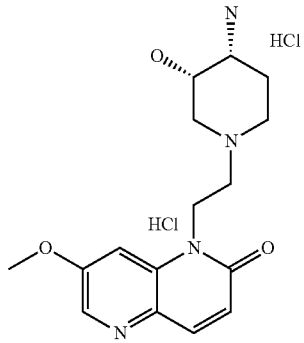

1-{2-[(3S,4R)-4-Amino-3-hydroxy-1-piperidinyl]ethyl}-7-(methyloxy)-1,5-naphthyridin-2(1H)-one dihydrochloride This was prepared from Intermediate 36 (223 mg) using a procedure analogous to that described for Intermediate 31 to give 209 mg of the title compound. [ES MS] m/z 319 (MH$^+$).

Intermediate 38

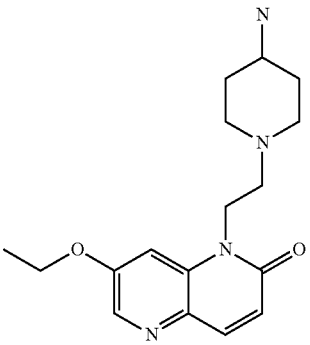

1-[2-(4-Amino-1-piperidinyl)ethyl]-7-(ethyloxy)-1,5-naphthyridin-2(1H)-one

Sodium hydride (124 mg) was added to a mixture of 1,4-dioxane (2 ml) and EtOH (2 ml) and it was stirred at room temperature for 5 minutes. Intermediate 21 (300 mg) was added and the mixture was microwave-heated to 160° C. for 10 minutes. H$_2$O was added and it was acidified with 2N HCl. The aqueous phase was washed with CH$_2$Cl$_2$/MeOH 10%, pH was adjusted to 11 with aqueous 2N NaOH. The aqueous layer was extracted with a mixture of $CH_2Cl_2$/MeOH 9:1, dried over $Na_2SO_4$ and concentrated under vacuum to give 255 mg of the title compound as a yellow oil. $^1$H-NMR (δ, ppm, DMSO-$d_6$): 8.25 (d, 1H), 7.84 (d, 1H), 7.38 (d, 1H), 6.63 (d, 1H), 4.34-4.22 (m, 4H), 2.88-2.84 (m, 2H), 2.05-1.97 (m, 2H), 1.65-1.61 (m, 2H), 1.40 (t, 3H), 1.21-1.09 (m, 2H). [ES MS] m/z 317 (MH$^+$).

Intermediate 39

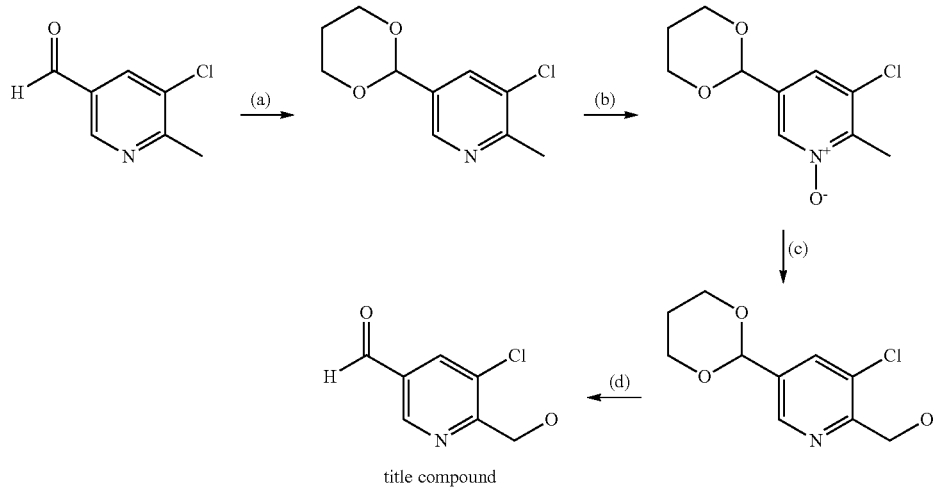

5-Chloro-6-(hydroxymethyl)-3-pyridinecarbaldehyde (a) 3-Chloro-5-(1,3-dioxolan-2-yl)-2-methylpyridine p-Toluenesulfonic acid (5.53 mg, 0.032 mmol) was added to a mixture of 5-chloro-6-methyl-3-pyridinecarbaldehyde (for a synthesis see WO20006/137485 A1 Example 256) (250 mg, 1.607 mmol), ethylene glycol (179 μl, 3.21 mmol), and toluene (8 ml) and the mixture was heated under reflux as water was azeotropically removed (Dean-Stark). The progression was monitored by TLC (50% hexane:EtOAc) and HPLC. More ethylene glycol (180 μl) and TsOH (3 mg) were added and after 46 hr full conversion was observed by HPLC. 10% Na2CO3 and EtOAc were added. Extraction, drying (MgSO4), and filtration afforded 3-chloro-5-(1,3-dioxolan-2-yl)-2-methylpyridine (274.3 mg, 86%) pure enough to be used in the next step.

$^1$H-NMR (δ, ppm, CDCl$_3$): 8.46 (s, 1H), 7.76 (s, 1H), 5.83 (s, 1H), 4.16-4.02 (s, 4H), 2.65 (s, 3H). [ES MS] m/z 200 (MH$^+$).

(b) 3-Chloro-5-(1,3-dioxolan-2-yl)-2-methylpyridine 1-oxide m-CPBA (626 mg, 2.72 mmol) was added to a suspension of 3-chloro-5-(1,3-dioxolan-2-yl)-2-methylpyridine (271.4 mg, 1.359 mmol) and NaHCO3 (343 mg, 4.08 mmol) in DCM (3 ml) and stirred at room temperature. After 21 h, HPLC showed full conversion. DCM and 1M NaOH were added. It was extracted, dried (MgSO4), filtered, and concentrated yielding 3-chloro-5-(1,3-dioxolan-2-yl)-2-methylpyridine 1-oxide (228 mg, 78%) as a pale yellow oil pure enough to be used in the next step.

$^1$H-NMR (δ, ppm, CDCl$_3$): 8.33 (s, 1H), 7.38 (s, 1H), 5.80 (s, 1H), 4.05 (s, 4H), 2.64 (s, 3H). [ES MS] m/z 216 (MH$^+$).

(c) [3-Chloro-5-(1,3-dioxolan-2-yl)-2-pyridinyl]methanol

Trifluoroacetic anhydride (231 μl, 1.635 mmol) was added to a solution of 3-chloro-5-(1,3-dioxolan-2-yl)-2-methylpyridine 1-oxide (225 mg, 1.043 mmol) in DCM (4 ml) at 0° C. and the mixture was stirred at room temperature for 48 h. Full conversion was observed by HPLC. MeOH (0.5 ml, 12.36 mmol) was added and, after stirring for 10 min, DCM and 10% Na2CO3 solution were added. Extraction, drying (MgSO$_4$), and filtration afforded 223.2 mg of crude material. Purification by flash chromatography using Flashmaster II, a 5 g silica gel cartridge, and mixtures of hexane and EtOAc as eluent afforded [3-chloro-5-(1,3-dioxolan-2-yl)-2-pyridinyl]methanol (142.7 mg, 63%) as a yellow oil.

$^1$H-NMR (δ, ppm, CDCl$_3$): 8.57 (s, 1H), 7.82 (s, 1H), 5.88 (s, 1H), 4.82 (s, 2H), 4.18-4.04 (m, 4H). [ES MS] m/z 216 (MH$^+$).

(d) Title Compound:
5-Chloro-6-(hydroxymethyl)-3-pyridinecarbaldehyde

Oxalic acid (415 mg, 3.29 mmol) was added to a mixture of [3-chloro-5-(1,3-dioxolan-2-yl)-2-pyridinyl]methanol (142 mg, 0.659 mmol), acetone (7.5 ml), and water (7.5 ml) at room temperature and heated under reflux. After 2.5 h, HPLC showed full conversion.

Cooled to rt, basified with 1M NaOH, extracted with TBME, dried (MgSO4), filtered and concentrated to give 139 mg of crude material. Purification by flash chromatography using Flashmaster II, a 5 g silica gel cartridge, and mixtures of DCM and MeOH as eluent afforded impure product. Repurification by manual flash chromatography using a 1 g silica gel cartridge, and mixtures of hexane and EtOAc as eluent afforded 5-chloro-6-(hydroxymethyl)-3-pyridinecarbaldehyde (11.3 mg, 10%) as a white solid.

$^1$H-NMRδ, ppm, CDCl$_3$): 10.12 (s, 1H), 8.95 (s, 1H), 8.17 (s, 1H), 4.90 (s, 2H), [ES MS] m/z 172 (MH$^+$).

Intermediate 40

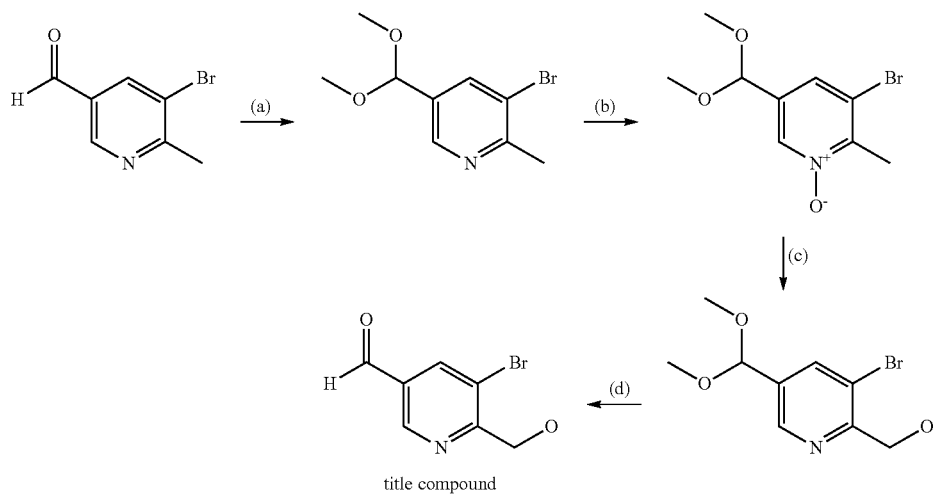

title compound

5-Bromo-6-(hydroxymethyl)-3-pyridinecarbaldehyde (a)
5-[Bis(methyloxy)methyl]-3-bromo-2-methylpyridine In a sealed tube charged with a solution of 5-bromo-6-methyl-3-pyridinecarbaldehyde (for a synthesis see PB62797 Intermediate 69) (191 mg, 0.955 mmol) in MeOH (15 ml) was added trimethyl orthoformate (1.045 ml, 9.55 mmol) and HCl (4M solution in 1,4-dioxane, 0.573 ml, 2.292 mmol). The reaction mixture was stirred at 70° C. for 2 h 30 min. The solution was concentrated under vacuum and the residue was diluted with saturated NaHCO$_3$ and EtOAc. The organic phase was extracted, dried over anhydrous Na$_2$SO$_4$ and concentrated under reduced pressure to give a pale oil. The crude was purified by flash chromatography using a 5 g Merck silica gel cartridge, and EtOAc/Hexane 1/9 as eluent to give 5-[bis(methyloxy)methyl]-3-bromo-2-methylpyridine (129.5 mg, 52%) as a yellow oil pure enough to be used in the next step.
$^1$H-NMR (δ, ppm, CDCl$_3$): 8.48 (s, 1H), 7.92 (s, 1H), 5.42 (s, 1H), 3.33 (s, 6H), 2.68 (s, 3H). [ES MS] m/z 246 (MH$^+$).

(b)
5-[Bis(methyloxy)methyl]-3-bromo-2-methylpyridine 1-oxide m-CPBA (242 mg, 1.052 mmol) was added to a suspension of 5-[bis(methyloxy)methyl]-3-bromo-2-methylpyridine (129.5 mg, 0.526 mmol) and NaHCO$_3$ (133 mg, 1.579 mmol) in DCM (5 ml). The mixture was stirred at room temperature overnight. To the resulting white suspension was added DCM and 1N NaOH. The organic phase was extracted twice, washed with sat. NaCl, dried over anhydrous MgSO$_4$ and concentrated to give 5-[bis(methyloxy)methyl]-3-chloro-2-methylpyridine 1-oxide (118 mg, 81%) as a yellow oil pure enough to be used in the next step.
$^1$H-NMR (δ, ppm, CDCl$_3$): 8.42 (s, 1H), 7.62 (s, 1H), 5.37 (s, 1H), 3.33 (s, 6H), 2.73 (s, 3H). [ES MS] m/z 262 (MH$^+$).

(c) {5-[Bis(methyloxy)methyl]-3-bromo-2-pyridinyl}methanol

Trifluoroacetic anhydride (0.191 mL, 1.353 mmol) was added to a solution of 5-[bis(methyloxy)methyl]-3-bromo-2-methylpyridine 1-oxide (118.2 mg, 0.451 mmol) in EtOAc (3 mL) at 0° C. and the mixture was heated at 77° C. in a sealed tube for 6 h and at room temperature overnight. Methanol (0.262 mL, 6.47 mmol) was added and the mixture was stirred at room temperature, and after stirring for 20 min, DCM and 10% Na$_2$CO$_3$ solution were added. Extraction, drying (Na$_2$SO$_4$), and filtration afforded {5-[bis(methyloxy)methyl]-3-bromo-2-pyridinyl}methanol (98 mg, 83%) as a brown oil pure enough to be used in the next step.
$^1$H-NMR (δ, ppm, CDCl$_3$): 8.57 (s, 1H), 7.97 (s, 1H), 5.48 (s, 1H), 4.75 (s, 2H), 3.33 (s, 6H). [ES MS] m/z 262 (MH$^+$).

(d)
5-Bromo-6-(hydroxymethyl)-3-pyridinecarbaldehyde

A mixture of {5-[bis(methyloxy)methyl]-3-bromo-2-pyridinyl}methanol (98 mg, 0.374 mmol) and 1N HCl (3.26 mL, 3.26 mmol) in DCM (5 mL) was stirred overnight. DCM and 1M NaOH solution were added. Extraction, drying (Na$_2$SO$_4$), and filtration afforded 5-bromo-6-(hydroxymethyl)-3-pyridinecarbaldehyde (70 mg, 87%) as a brown oil pure enough to be used in the next step.
$^1$H-NMR (δ, ppm, CDCl$_3$): 8.57 (s, 1H), 7.97 (s, 1H), 5.48 (s, 1H), 4.75 (s, 2H), 3.33 (s, 6H). [ES MS] m/z 215 (MH$^+$).

PREPARATION OF EXAMPLES

Example 1

1-{2-[4-({[5-chloro-6-(hydroxymethyl)-3-pyridinyl]methyl}amino)-1-piperidinyl]ethyl}-7-fluoro-1,5-naphthyridin-2(1H)-one

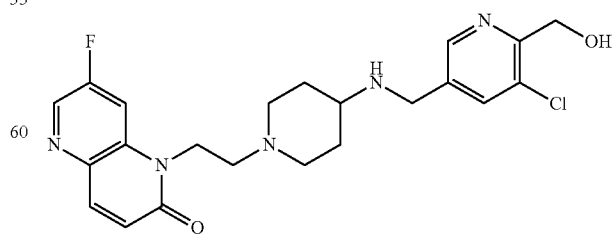

A mixture of 1-[2-(4-amino-1-piperidinyl)ethyl]-7-fluoro-1,5-naphthyridin-2(1H)-one (Intermediate 21: 38.9 mg, 0.134 mmol) and 5-chloro-6-(hydroxymethyl)-3-pyridinecarbaldehyde (Intermediate 39: 23 mg, 0.134 mmol) in 1,2-Dichloroethane (2.5 ml) was stirred under N2 at room temperature for 1 h. Then, sodium triacetoxy borohydride (85 mg, 0.402 mmol) was added and the mixture was stirred at RT overnight. LCMS showed desired compound and imine. An excess of sodium triacetoxy borohydride (85 mg, 0.401 mmol) was added and the mixture was stirred at rt 6 h. LCMS showed desired compound and imine. An excess of sodium triacetoxy borohydride (85 mg, 0.401 mmol) was added. The mixture was stirred at room temperature overnight. LCMS showed desired compound and imine. An excess of sodium triacetoxy borohydride (85 mg, 0.401 mmol) was added and the mixture was stirred at room temperature overnight. LCMS did not show imine and showed desired compound. NaHCO$_3$ sat. was added and the aqueous phase was extracted twice with DCM. The combined organic phases were washed with sat. NaCl, dried over anhydrous Na$_2$SO$_4$ and concentrated under reduced pressure. The residue was purified by Flash-Master chromatography on a 2 g silica gel cartridge using DCM/MeOH 95:5 as eluent to obtain two fractions. The first was 9 mg of white solid consistent with the desired compound by HNMR. The second was 4 mg white solid consistent with desired compound but not enough pure by HNMR and LCMS. This second fraction was discarded.

$^1$H-NMR (δ, ppm, CDCl$_3$): 8.42 (bs, 2H); 7.89 (d, 1H); 7.74 (s, 1H); 7.55 (d, 1H); 6.86 (d, 1H); 4.78 (s, 2H); 4.33 (t, 2H); 3.85 (s, 2H); 2.97 (d, 2H); 2.66 (t, 2H); 2.56-2.52 (m, 1H); 2.21 (t, 2H); 1.92 (d, 2H); 1.47-1.40 (m, 2H). [ES MS] m/z 446 (MH$^+$).

Example 2

1-{2-[4-({[5-chloro-6-(hydroxymethyl)-3-pyridinyl]methyl}amino)-1-piperidinyl]ethyl}-7-fluoro-1,5-naphthyridin-2(1H)-one hydrochloride

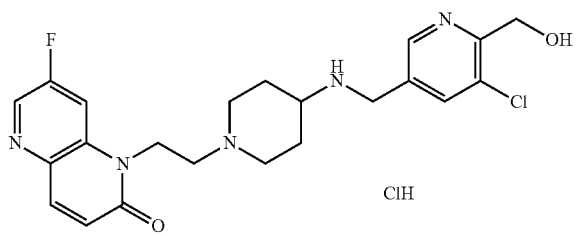

To a solution of 1-{2-[4-({[5-chloro-6-(hydroxymethyl)-3-pyridinyl]methyl}amino)-1-piperidinyl]ethyl}-7-fluoro-1,5-naphthyridin-2(1H)-one (Example 1: 163.2 mg, 0.366 mmol) in Dichloromethane (2.5 ml) at 0° C. was added HCl (4M in 1,4-dioxane) (0.092 ml, 0.369 mmol). The reaction mixture was stirred at RT for 30 min, the solvent was evaporated under vacuum and the crude was dispersed in hexane/DCM. The precipitated solid was isolated by filtration under vacuum and washed with DCM and hexane. The obtained solid was dried overnight at 40° C. under vacuum to give 1-{2-[4-({[5-chloro-6-(hydroxymethyl)-3-pyridinyl]methyl}amino)-1-piperidinyl]ethyl}-7-fluoro-1,5-naphthyridin-2(1H)-one hydrochloride (137 mg, 0.281 mmol, 77% yield) as a white solid.

$^1$H-NMR (δ, ppm, DMSO-d6): 9.06 (bs, 1H); 8.62-8.57 (m, 2H); 8.14 (s, 1H); 8.06 (d, 1H); 7.96 (d, 1H); 6.84 (d, 1H); 5.31 (t, 1H); 4.64 (d, 2H); 4.36 (bs, 2H); 4.17 (bs, 2H); 3.08-2.97 (m, 3H); 2.60 (bs, 4H); 2.66 (t, 2H); 2.56-2.52 (m, 1H); 2.21 (t, 2H); 1.92 (d, 2H); 1.47-1.40 (m, 2H). [ES MS] m/z 446 (MH$^+$).

Example 3

1-{2-[(3R,4S)-4-({[5-chloro-6-(hydroxymethyl)-3-pyridinyl]methyl}amino)-3-hydroxy-1-piperidinyl]ethyl}-7-fluoro-1,5-naphthyridin-2(1H)-one

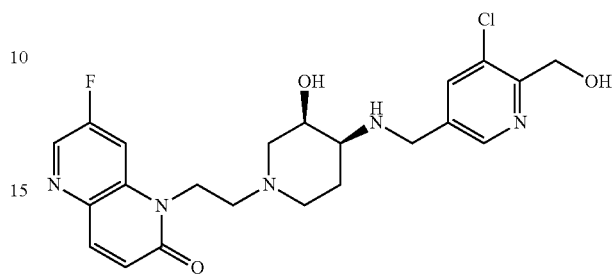

A mixture of 1-{2-[(3R,4S)-4-amino-3-hydroxy-1-piperidinyl]ethyl}-7-fluoro-1,5-naphthyridin-2(1H)-one (Intermediate 31 as a free base: 60 mg, 0.196 mmol) and 5-chloro-6-(hydroxymethyl)-3-pyridinecarbaldehyde (Intermediate 39: 33.6 mg, 0.196 mmol) in DCE (5 ml) and Methanol (0.5 ml) was stirred at rt for 5 h. LCMS showed desired compound Rt 2.16 [M+H]+ 460 and not starting material, sodium triacetoxy borohydride (125 mg, 0.588 mmol) was added. The mixture was stirred under nitrogen at room temperature overnight. LCMS showed desired compound and imine. An excess of sodium triacetoxy borohydride (62.3 mg, 0.294 mmol) was added. The mixture was stirred at room temperature for 3 h. Full conversion to the amine was observed by LCMS desired compound Rt 2.02 [M+H]+ 462. It was quenched with saturated NaHCO$_3$, extracted with dichloromethane, dried (MgSO$_4$), filtered, and concentrated affording 78.5 mg of crude material. Purification by manual flash chromatography using a 5 g Merck silica gel cartridge, and DCM/MeOH 9/1 as eluent afforded 1-{2-[(3R,4S)-4-({[5-chloro-6-(hydroxymethyl)-3-pyridinyl]methyl}amino)-3-hydroxy-1-piperidinyl]ethyl}-7-fluoro-1,5-naphthyridin-2(1H)-one (35 mg, 0.072 mmol, 36.8% yield) as a white solid.

$^1$H-NMR (δ, ppm, CDCl$_3$): 8.41-8.39 (m, 2H); 7.88 (d, 1H); 7.81 (s, 1H); 7.60 (bd, 1H); 6.82 (d, 1H); 4.73 (s, 2H); 4.49-4.39 (m, 1H); 4.24-4.17 (m, 1H); 3.94-3.85 (m, 2H); 3.37-3.33 (m, 1H); 3.15 (bd, 1H); 2.86 (bd, 1H); 2.68-2.65 (m, 3H); 2.36-2.21 (m, 2H); 1.79-1.65 (m, 2H). [ES MS] m/z 462 (MH$^+$).

Example 4

1-{2-[(3R,4S)-4-({[5-chloro-6-(hydroxymethyl)-3-pyridinyl]methyl}amino)-3-hydroxy-1-piperidinyl]ethyl}-7-fluoro-1,5-naphthyridin-2(1H)-one hydrochloride

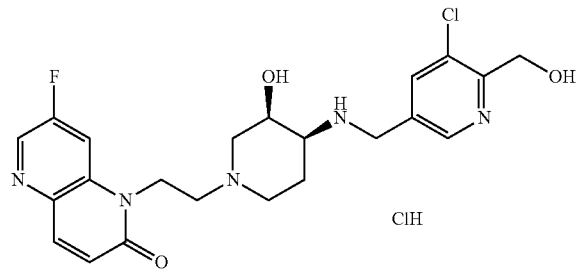

To a solution of 1-{2-[(3R,4S)-4-({[5-chloro-6-(hydroxymethyl)-3-pyridinyl]methyl}amino)-3-hydroxy-1-piperidinyl]ethyl}-7-fluoro-1,5-naphthyridin-2(1H)-one (Example 3: 19.5 mg, 0.042 mmol) in DCM (2 ml) at 0° C. was added HCl (4M in 1,4-dioxane) (10.64 μl, 0.043 mmol). The reaction mixture was stirred at RT for 30 min, the solvent was evaporated under vacuum and the crude was dispersed in hexane/DCM. The precipitated solid was isolated by filtration under vacuum and washed with DCM and hexane. The obtained solid was dried overnight at 40° C. under vacuum to give 1-{2-[(3R,4S)-4-({[5-chloro-6-(hydroxymethyl)-3-pyridinyl]methyl}amino)-3-hydroxy-1-piperidinyl]ethyl}-7-fluoro-1,5-naphthyridin-2(1H)-one hydrochloride (19.5 mg, 0.039 mmol, 92% yield) as a white solid.

$^1$H-NMR (δ, ppm, CD$_3$OD): 8.55-8.50 (m, 2H); 8.03-7.98 (m, 3H); 6.88 (d, 1H); 4.93-4.80 (m, 3H); 4.58-4.35 (m, 3H); 4.17-4.05 (m, 3H); 3.24-3.21 (m, 1H); 3.09-2.99 (m, 2H); 2.46-2.30 (m, 2H); 1.93-1.84 (m, 2H). [ES MS] m/z 462 (MH$^+$).

Example 5

1-{2-[4-({[5-chloro-6-(hydroxymethyl)-3-pyridinyl]methyl}amino)-1-piperidinyl]ethyl}-7-(methyloxy)-1,5-naphthyridin-2(1H)-one

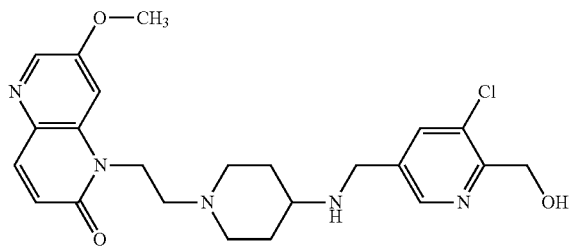

1-[2-(4-amino-1-piperidinyl)ethyl]-7-(methyloxy)-1,5-naphthyridin-2(1H)-one (Intermediate 29: 100 mg, 0.331 mmol) was dissolved in a mixture of Dichloromethane (DCM) (4 mL) and Methanol (0.444 mL). Aldehyde 5-chloro-6-(hydroxymethyl)-3-pyridinecarbaldehyde (Intermediate 39: 56.7 mg, 0.331 mmol) was added and the mixture was left at room temp. for 3 hours. Then sodium triacetoxy borohydride (210 mg, 0.992 mmol) was added and after 2 hours 2 more eq. of triacetoxy borohydride were added leaving the reaction under stirring overnight. LCMS overnight showed still imine remaining so 3 eq more of sodium triacetoxy borohydride were added and 2 eq more after 3 hours leaving the reaction overnight. Next morning 2 more eq. of sodium triacetoxy borohydride were added and after 3H reaction was stopped. Volatiles were removed under vacuum and the corresponding crude was diluted with DCM and washed with NaHCO3 several times. Organic layers were dried over Na2SO4, filtered and volatiles removed under vacuum. Corresponding crude was purified by flash master chromatography. Si II, 5 g. DCM/MeOH (0-30%), to obtain a solid which was left in the oven overnight to afford 45 mg of the final compound as a pale yellow solid.

$^1$H-NMR (δ, ppm, CDCl3): 8.41 (s, 1H); 8.28 (s, 1H); 7.83 (d, 1H); 7.73 (s, 1H); 7.22 (s, 1H); 6.75 (d, 1H); 4.78 (s, 2H); 4.47-4.29 (m, 2H); 3.98 (s, 3H); 3.85 (s, 2H); 3.06-2.93 (m, 2H); 2.72-2.61 (m, 2H); 2.59-2.48 (m, 1H); 2.29-2.13 (m, 2H); 1.98-1.85 (m, 2H); 1.59-1.37 (m, 2H). [ES MS] m/z 457 (MHδ).

Example 6

1-{2-[4-({[5-bromo-6-(hydroxymethyl)-3-pyridinyl]methyl}amino)-1-piperidinyl]ethyl}-7-fluoro-1,5-naphthyridin-2(1H)-one

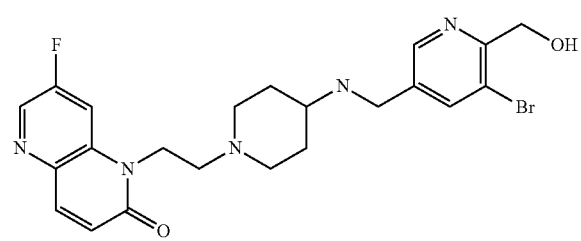

A mixture of 1-[2-(4-amino-1-piperidinyl)ethyl]-7-fluoro-1,5-naphthyridin-2(1H)-one (Intermediate 21: 50.9 mg, 0.175 mmol) and 5-bromo-6-(hydroxymethyl)-3-pyridinecarbaldehyde (Intermediate 40: 37.9 mg, 0.175 mmol) in DCE (3 ml) was stirred under N$_2$ at room temperature overnight. Then, sodium triacetoxyborohydride (112 mg, 0.526 mmol) was added and the mixture was stirred for 8 h at RT overnight. Saturated NaHCO$_3$ was added and the aqueous phase was extracted twice with DCM. The combined organic phases were dried over anhydrous Na$_2$SO$_4$ and concentrated under reduced pressure. The residue was purified by FlashMaster chromatography on a 2 g silica gel cartridge using DCM/MeOH 9/1 as eluent to give 1-{2-[4-({[5-bromo-6-(hydroxymethyl)-3-pyridinyl]methyl}amino)-1-piperidinyl]ethyl}-7-fluoro-1,5-naphthyridin-2(1H)-one (21.5 mg, 25%) as a white solid.

$^1$H-NMR (δ, ppm, CDCl$_3$): 8.42 (d, 2H); 7.90-7.86 (m, 2H); 7.64 (d, 1H); 6.83 (d, 1H); 4.70 (s, 2H); 4.34 (t, 2H); 3.81 (s, 2H); 3.00 (bd, 2H); 2.65 (t, 2H); 2.55 (bs, 1H); 2.24 (bd, 2H); 1.95-1.84 (m, 2H); 1.49-1.43 (m, 2H). [ES MS] m/z 490 (MH$^+$).

Example 7

1-{2-[(3R,4S)-4-({[5-chloro-6-(hydroxymethyl)-3-pyridinyl]methyl}amino)-3-hydroxy-1-piperidinyl]ethyl}-7-(methyloxy)-1,5-naphthyridin-2(1H)-one

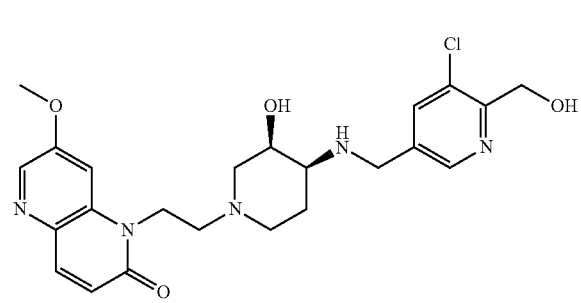

A mixture of 1-{2-[(3R,4S)-4-amino-3-hydroxy-1-piperidinyl]ethyl}-7-(methyloxy)-1,5-naphthyridin-2(1H)-one (Intermediate 33 as a free base: 200 mg, 0.628 mmol) and 5-chloro-6-(hydroxymethyl)-3-pyridinecarbaldehyde (108 mg, 0.628 mmol) in DCE (10 ml) and Methanol (0.5 ml) was stirred at room temperature overnight. Sodium triacetoxyborohydride (399 mg, 1.885 mmol) was added. The mixture was stirred under $N_2$ at rt for 6 h. LCMS showed imine and desired compound. An excess of sodium triacetoxyborohydride (399 mg, 1.885 mmol) was added. The mixture was stirred overnight. Full conversion to the amine was observed by LCMS. It was quenched with saturated $NaHCO_3$, extracted with DCM/MeOH 9/1, dried ($MgSO_4$), filtered, and concentrated affording 242 mg of crude material. Purification by manual flash chromatography using a 5 g Merck silica gel cartridge, and DCM/MeOH 9/1 as eluent afforded 1-{2-[(3R,4S)-4-({[5-chloro-6-(hydroxymethyl)-3-pyridinyl]methyl}amino)-3-hydroxy-1-piperidinyl]ethyl}-7-(methyloxy)-1,5-naphthyridin-2(1H)-one (179.8 mg, 0.360 mmol, 57% yield) as a white solid.

$^1$H-NMR (δ, ppm, $CDCl_3$): 8.44 (s, 1H); 8.30 (s, 1H); 7.86 (d, 1H); 7.78 (s, 1H); 7.15 (s, 1H); 6.75 (d, 1H); 4.77 (s, 2H); 4.56-4.51 (m, 1H); 4.28 (bs, 1H); 4.00 (s, 3H); 3.96-3.82 (m, 3H); 3.22 (bd, 1H); 2.92 (bd, 1H); 2.77-2.74 (m, 2H); 2.53 (bd, 1H); 2.36 (bd, 1H); 2.27 (bs, 1H); 1.78-1.67 (m, 2H). [ES MS] m/z 474 ($MH^+$).

Example 8

1-{2-[(3R,4S)-4-({[5-chloro-6-(hydroxymethyl)-3-pyridinyl]methyl}amino)-3-hydroxy-1-piperidinyl]ethyl}-7-(methyloxy)-1,5-naphthyridin-2(1H)-one hydrochloride

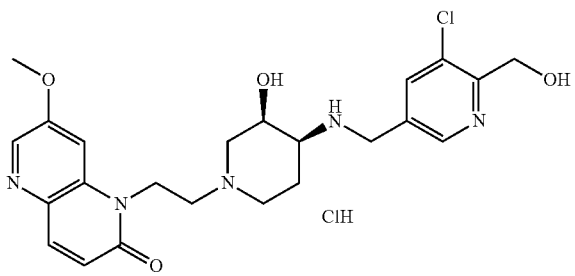

To a solution of 1-{2-[(3R,4S)-4-({[5-chloro-6-(hydroxymethyl)-3-pyridinyl]methyl}amino)-3-hydroxy-1-piperidinyl]ethyl}-7-(methyloxy)-1,5-naphthyridin-2(1H)-one (Example 7 above: 179.8 mg, 0.379 mmol) in DCM (2.5 ml) at 0° C. was added HCl (1M in diethyl ether) (0.417 ml, 0.417 mmol). The reaction mixture was stirred at rt for 30 min, the solvent was evaporated under vacuum and the crude was dispersed in hexane/DCM. The precipitated solid was isolated by filtration under vacuum and washed with DCM and hexane. The obtained solid was dried overnight at 40° C. under vacuum to give 1-{2-[(3R,4S)-4-({[5-chloro-6-(hydroxymethyl)-3-pyridinyl]methyl}amino)-3-hydroxy-1-piperidinyl]ethyl}-7-(methyloxy)-1,5-naphthyridin-2(1H)-one hydrochloride (143.7 mg, 0.282 mmol, 74.2% yield) as a white solid.

$^1$H-NMR (δ, ppm, DMSO-$d_6$): 9.04 (bs, 1H); 8.61 (bs, 1H); 8.31 (bs, 1H); 8.13 (bs, 1H); 7.89 (d, 1H); 7.45 (bs, 1H); 6.68 (d, 1H); 5.30 (bs, 1H); 5.21 (bs, 1H); 4.64 (d, 2H); 4.42 (bs, 2H); 4.17 (bs, 2H); 4.00 (bs, 4H); 3.04 (bs, 3H); 2.66 (bs, 1H); 2.32 (bs, 2H); 1.82 (m, 2H). [ES MS] m/z 474 ($MH^+$).

BIOLOGICAL ACTIVITY

*Mycobacterium tuberculosis* H37Rv Inhibition Assay

The measurement of the minimum inhibitory concentration (MIC) for each tested compound was performed in 96 wells flat-bottom, polystyrene microtiter plates. Ten two-fold drug dilutions in neat DMSO starting at 400 μM were performed. Five μl of these drug solutions were added to 95 μl of Middlebrook 7H9 medium. (Lines A-H, rows 1-10 of the plate layout). Isoniazid was used as a positive control, 8 two-fold dilution of Isoniazid starting at 160 μgml$^{-1}$ was prepared and 5 μl of this control curve was added to 95 μl of Middlebrook 7H9 medium (Difco catalogue ref. 271310). (Row 11, lines A-H). Five μl of neat DMSO were added to row 12 (growth and Blank controls).

The inoculum was standardised to approximately 1×10$^7$ cfu/ml and diluted 1 in 100 in Middlebrook 7H9 broth (Middlebrook ADC enrichment, a dehydrated culture media which supports growth of mycobacterial species available from Becton Dickinson Catalogue Ref. 211887), to produce the final inoculum of H37Rv strain (ATCC25618). One hundred μl of this inoculum was added to the entire plate but G-12 and H-12 wells (Blank controls). All plates were placed in a sealed box to prevent drying out of the peripheral wells and they were incubated at 37° C. without shaking for six days. A resazurin solution was prepared by dissolving one tablet of resazurin (Resazurin Tablets for Milk Testing; Ref 330884Y VWR International Ltd) in 30 ml sterile PBS (phosphate buffered saline). 25 μl of this solution was added to each well. Fluorescence was measured (Spectramax M5 Molecular Devices, Excitation 530 nm, Emission 590 nm) after 48 hours to determine the MIC value.

Results of the *Mycobacterium tuberculosis* H37Rv Inhibition Assay

Examples 1 to 6 were tested in the *Mycobacterium tuberculosis* H37Rv inhibition assay. All of these Examples showed an MIC value of 0.3 μg/ml or lower.

The invention claimed is:
1. A compound of Formula (I) or a pharmaceutically acceptable salt thereof:

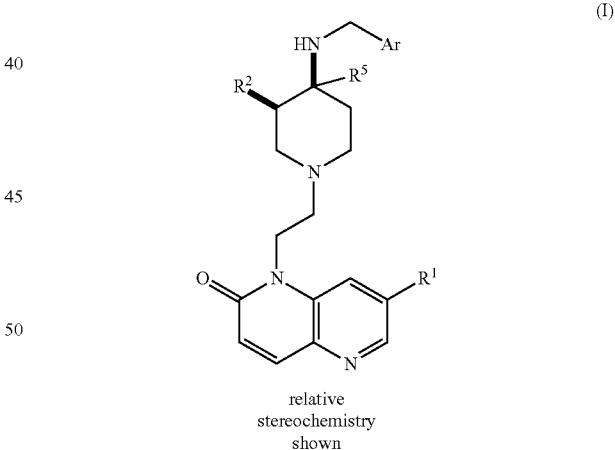

relative stereochemistry shown wherein in Formula (I):
$R^1$ represents hydrogen; halo; or $C_{1-3}$alkoxy-;
$R^2$ represents hydrogen or hydroxy;
Ar represents a group selected from: phenyl, pyridinyl, pyridazinyl, pyrimidinyl, pyrazinyl, thiazolyl, furanyl, imidazolyl and thiophenyl;
wherein
Ar is substituted by a first substituent $R^3$, wherein $R^3$ represents $C_{1-5}$ hydroxyalkyl;
Ar is optionally substituted by a second substituent $R^4$ selected from halo, $CF_3$, $C_{1-3}$ alkyl, nitro and $C_{1-3}$ alkoxy-;

and if $R^2$ is hydrogen then $R^5$ is hydrogen or $C_{1-3}$ alkyl, and if $R^2$ is hydroxyl then $R^5$ is hydrogen.

2. A compound of Formula (I) or a pharmaceutically acceptable salt thereof as claimed in claim 1 wherein Ar represents a group selected from: phenyl, pyridazinyl, pyridiminyl, pyrazinyl, thiazolyl, furanyl and thiophenyl.

3. A compound of Formula (I) or a pharmaceutically acceptable salt thereof as claimed in claim 1 wherein Ar is pyridinyl.

4. A compound of Formula (I) or a pharmaceutically acceptable salt thereof as claimed in claim 3 wherein Ar is a 3-pyridinyl substituent and the $C_{1-5}$ hydroxyalkyl substituent $R^3$ is in the 6-position relative to the ring nitrogen.

5. A compound of Formula (I) or a pharmaceutically acceptable salt thereof as claimed in claim 1 wherein the $C_{1-5}$ hydroxyalkyl substituent $R^3$ is hydroxymethyl.

6. A compound of Formula (I) or a pharmaceutically acceptable salt thereof as claimed in claim 1 wherein the substituent $R^4$ is present and is halo.

7. A compound of Formula (I) or a pharmaceutically acceptable salt thereof as claimed in claim 6 wherein $R^4$ is present and is chloro.

8. A compound of Formula (I) or a pharmaceutically acceptable salt thereof according to claim 5, wherein Ar is 5-chloro-6-(hydroxymethyl)-3-pyridinyl.

9. A compound of Formula (I) or a pharmaceutically acceptable salt thereof as claimed in claim 1 wherein $R^2$ represents hydroxy, and the absolute stereochemistry of the compound of Formula (I), or a pharmaceutically acceptable salt thereof, is:

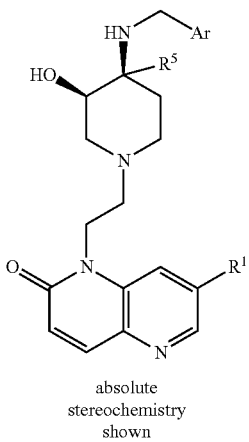

absolute stereochemistry shown

10. A compound of Formula (I) or a pharmaceutically acceptable salt thereof as claimed in claim 1 selected from:
1-{2-[4-({[5-chloro-6-(hydroxymethyl)-3-pyridinyl]methyl}amino)-1-piperidinyl]ethyl}-7-fluoro-1,5-naphthyridin-2(1H)-one;
1-{2-[4-({[5-chloro-6-(hydroxymethyl)-3-pyridinyl]methyl}amino)-1-piperidinyl]ethyl}-7-fluoro-1,5-naphthyridin-2(1H)-one hydrochloride;
1-{2-[(3R,4S)-4-({[5-chloro-6-(hydroxymethyl)-3-pyridinyl]methyl}amino)-3-hydroxy-1-piperidinyl]ethyl}-7-fluoro-1,5-naphthyridin-2(1H)-one;
1-{2-[(3R,4S)-4-({[5-chloro-6-(hydroxymethyl)-3-pyridinyl]methyl}amino)-3-hydroxy-1-piperidinyl]ethyl}-7-fluoro-1,5-naphthyridin-2(1H)-one hydrochloride;
1-{2-[4-({[5-chloro-6-(hydroxymethyl)-3-pyridinyl]methyl}amino)-1-piperidinyl]ethyl}-7-(methyloxy)-1,5-naphthyridin-2(1H)-one;
1-{2-[4-({[5-bromo-6-(hydroxymethyl)-3-pyridinyl]methyl}amino)-1-piperidinyl]ethyl}-7-fluoro-1,5-naphthyridin-2(1H)-one;
1-{2-[(3R,4S)-4-({[5-chloro-6-(hydroxymethyl)-3-pyridinyl]methyl}amino)-3-hydroxy-1-piperidinyl]ethyl}-7-(methyloxy)-1,5-naphthyridin-2(1H)-one;
and
1-{2-[(3R,4S)-4-({[5-chloro-6-(hydroxymethyl)-3-pyridinyl]methyl}amino)-3-hydroxy-1-piperidinyl]ethyl}-7-(methyloxy)-1,5-naphthyridin-2(1H)-one hydrochloride.

11. A pharmaceutical composition comprising a) a compound of Formula (I) or a pharmaceutically acceptable salt thereof as claimed in claim 1, and b) one or more pharmaceutically acceptable carriers, excipients or diluents.

12. A method of treatment of tuberculosis in a mammal which method comprises the administration to a mammal in need of such treatment an effective amount of a compound of Formula (I) or a pharmaceutically acceptable salt thereof as claimed in claim 1.

13. A method of treatment of bacterial infections in a mammal which method comprises the administration to a mammal in need of such treatment an effective amount of a compound of Formula (I) or a pharmaceutically acceptable salt thereof as claimed in claim 1.

14. A process for the preparation of a compound of Formula (I) according to claim 1, by a reaction between a compound of Formula (II), wherein $R^1$, $R^2$ and $R^5$ are as defined for Formula (I), or an acid salt of a compound of Formula (II) such as a hydrochloride salt, and an aldehyde of Formula (III), wherein Ar is as defined for Formula (I), according to the scheme below:

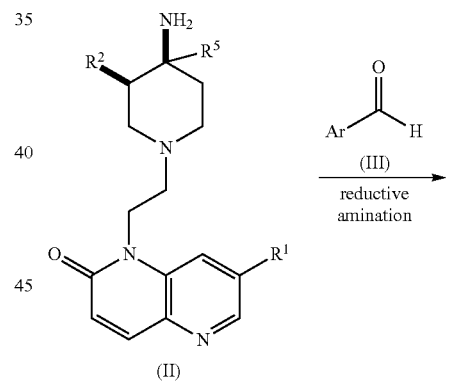

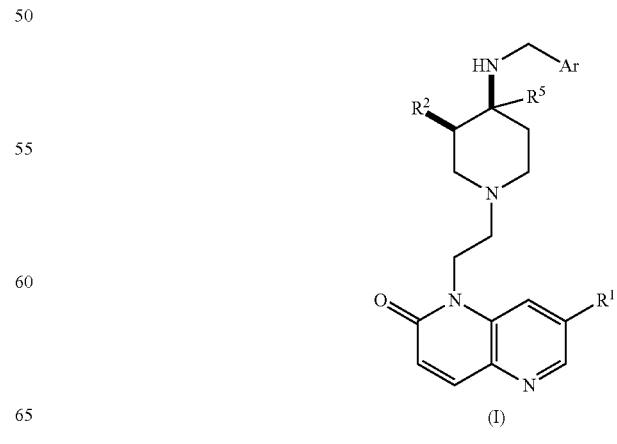

15. A process for the preparation of a compound of Formula (I) wherein $R^1$ and Ar are as defined for Formula (I) and $R^2$ is hydrogen, by a reaction between a compound of Formula (II), wherein $R^1$ is as defined for Formula (I) and $R^2$ is hydrogen, and an alkylating agent of Formula (IV), wherein hal is a halo substituent, according to the scheme below:

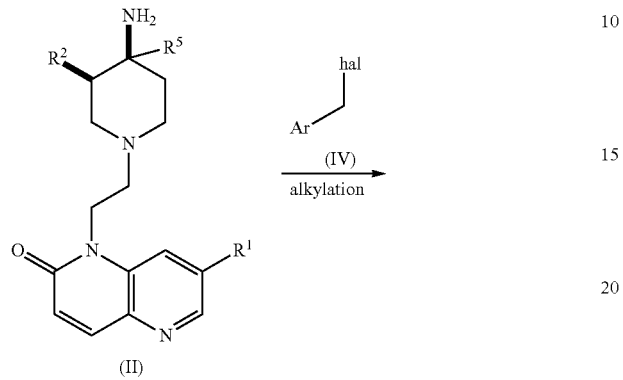

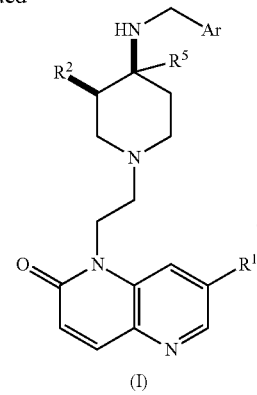

16. A combination comprising a) a compound of Formula (I) or a pharmaceutically acceptable salt thereof as claimed in claim 1, and b) one or more additional therapeutic agents.

17. The method of claim 12 wherein said mammal is a human.

18. The method of claim 13 wherein said mammal is a human.

* * * * *